US012716065B2

(12) United States Patent
Ichida et al.

(10) Patent No.: US 12,716,065 B2
(45) Date of Patent: Aug. 25, 2026

(54) ANTAGONISM AS A THERAPY FOR TDP-43 PROTEINOPATHIES

(71) Applicant: University of Southern California, Los Angeles, CA (US)

(72) Inventors: Justin Ichida, Los Angeles, CA (US); Gabriel Linares, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 931 days.

(21) Appl. No.: 17/793,554

(22) PCT Filed: Jan. 22, 2021

(86) PCT No.: PCT/US2021/014541

§ 371 (c)(1),
(2) Date: Jul. 18, 2022

(87) PCT Pub. No.: WO2021/150840

PCT Pub. Date: Jul. 29, 2021

(65) Prior Publication Data

US 2023/0066380 A1 Mar. 2, 2023

Related U.S. Application Data

(60) Provisional application No. 62/965,152, filed on Jan. 23, 2020.

(51) Int. Cl.
*C12N 15/113* (2010.01)
*A61P 25/28* (2006.01)

(52) U.S. Cl.
CPC ............ *C12N 15/113* (2013.01); *A61P 25/28* (2018.01); *C12N 2310/11* (2013.01); *C12N 2310/14* (2013.01); *C12N 2310/315* (2013.01); *C12N 2310/321* (2013.01); *C12N 2310/323* (2013.01); *C12N 2310/33* (2013.01)

(58) Field of Classification Search
None
See application file for complete search history.

(56) References Cited

U.S. PATENT DOCUMENTS

| | | | | |
|---|---|---|---|---|
| 6,703,541 | B1 | 3/2004 | Padegimas et al. | |
| 2004/0127694 | A1* | 7/2004 | Komeluk ............ | C12N 15/113 536/23.1 |
| 2005/0153917 | A1 | 7/2005 | Al-Mahmood et al. | |
| 2010/0190656 | A1 | 7/2010 | Li et al. | |
| 2012/0214865 | A1 | 8/2012 | Bennett et al. | |
| 2015/0038352 | A1 | 2/2015 | Cao et al. | |

FOREIGN PATENT DOCUMENTS

| | | | | |
|---|---|---|---|---|
| WO | WO 2004/092379 | | 10/2004 | |
| WO | 2005/042030 | A1 | 5/2005 | |
| WO | WO-2006047250 | A2 * | 5/2006 | ............. A61P 25/00 |
| WO | 2007/109097 | A2 | 9/2007 | |
| WO | 2016/024205 | A1 | 2/2016 | |
| WO | WO-2024163651 | A2 * | 8/2024 | .......... C12N 15/113 |

OTHER PUBLICATIONS

De Boer et al. J. Neurol Neurosurg Psychiatry; 92:86-95 (Year: 2021).*
Xu et al. Journal of Neuroscience Research 92:318-328 (Year: 2014).*
Zhou et al. Cell Mol Beurobiol 34:1023-1036 (Year: 2014).*
Bennett et al. Annu Rev Pharmacol Toxicol. 61:831-852 (Year: 2021).*
Hwang et al. Molecular Therapy Nucleic Acids vol. 35, pp. 1-15 (Year: 2024).*
Shi et al., "Overexpression of SYF2 promotes cell proliferation and correlates with poor prognosis in human breast cancer," Oncotarget, 8:88453-88463, 2017.
Young, Lee, International Search Report & Written Opinion, United States Patent & Trademark Office, PCT/US2021/014541, Jun. 4, 2021.
Romano, Alper, European Search Report, Application No. 21744099.9, European Patent Office, Dec. 8, 2023.
Baharlou, Simin, International Preliminary Report on Patentability and Written Opinion, The International Bureau of WIPO, PCT/US2021/014541, Aug. 4, 2022.

* cited by examiner

*Primary Examiner* — Brian Whiteman
(74) *Attorney, Agent, or Firm* — pH IP Law

(57) ABSTRACT

Disclosed is a method of treating a subject who has a neurological disease. In one aspect, the method includes a step of administering an effective dose of a SYF2 antisense or inhibitory nucleic acid to a subject in need thereof, thereby restoring nuclear localization of TDP-43.

24 Claims, 14 Drawing Sheets

Specification includes a Sequence Listing.

ALS Patients 4
2 Better neuron survival
0
-2 Worse neuron survival
-4

Drugs

Broadly-active drugs (including steroids)

sporadic C9

| Clue.io (Connectivity Map) analysis | | |
|---|---|---|
| name | description | median_tau_score |
| SYF2 | SYF2 homolog, RNA splicing factor (S. cerevisiae) | 77.32 |
| CD40 | Tumour necrosis factor (TNF) receptor family, CD40 molecule | 74.61 |
| RASSF1 | Ras association (RalGDS/AF-6) domain family member 1 | 74.35 |

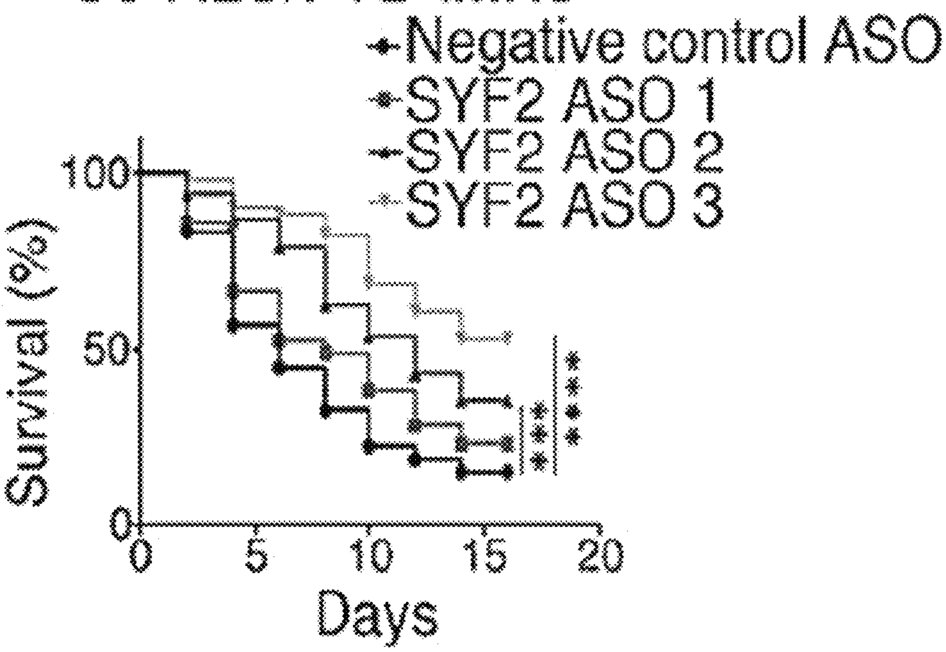
FIG. 3B
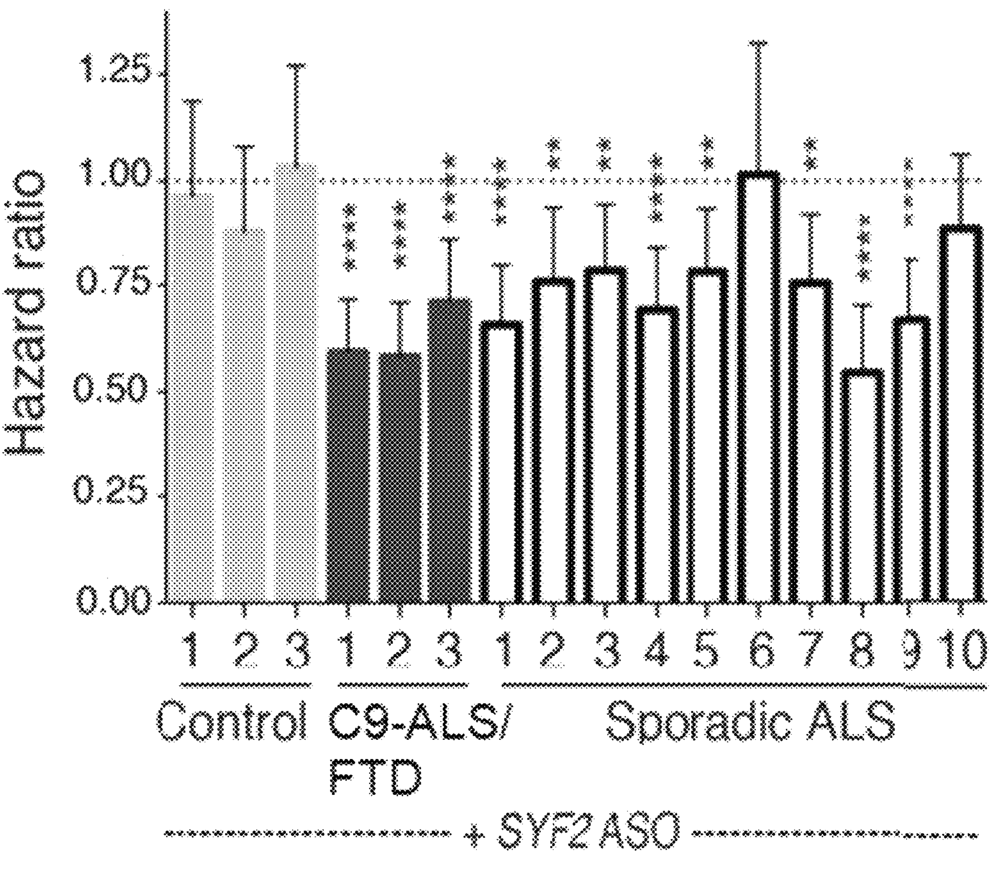
FIG. 3C

WT + NC ASO (n=11)
WT + SYF2 ASO (n=9)
TDP-43$^{Tg/Tg}$ + NC ASO (n=8)
TDP-43$^{Tg/Tg}$ + SYF2 ASO (n=8)
Tramor Score
Days

```
cttgttgccg gaagtgggaa gagagaaagg ttgtgatggc ggctatagct gcatccgagg 61
tgctggtgga cagcgcggag gaggggtccc tcgctgcggc ggcggagctg gccgctcaga 121
agcgcgaaca gagactgcgc aaattccggg agctgcacct gatgcggaat gaagctcgta 181
aattaaatca ccaggaagtt gtggaagaag ataaaagact aaaattacct gcaaattggg 241
aagccaaaaa agctcgtttg gagtgggaac taaaggaaga ggaaaagaaa aaggaatgtg 301
cggcaagagg agaagactat gagaaagtga agttgctgga gatcagtgca gaagatgcag 361
aaagatggga gaggaaaaag aagaggaaaa accctgatct gggattttca gattatgctg 421
ctgcccagtt acgccagtat catcggttga ccaagcagat caaacctgac atggaaacat 481
atgagagact gagagaaaaa catggagaag agtttttccc aacatccaat agtcttcttc 541
atggaacaca tgtgccttcc acagaggaaa ttgacaggat ggtcatagat ctggaaaaac 601
agattgaaaa acgagacaaa tatagccgga gacgtcctta taatgatgat gcagatatcg 661
actacattaa tgaaaggaat gccaaattca acaagaaagc tgaaagattc tatgggaaat 721
acacagctga aattaaacag aatttggaaa gaggaacagc tgtctaatcc cttcaagaac 781
tgtttataga agcttgagaa tggggtaaaa atttctgcta gcaaaatcaa gttctttttg 841
aaatttatc agtaatccag aatttagtag tccatgcctt ctcactcagc atttagaaat 901
aaaaatgtgg tttcttaaac gtatatcctt tcatgtatat ttccacattt ttgtgcttgg 961
atataagatg tatttcttgt agtgaagttg ttttgtaatc tactttgtat acattctaat 1021
tatattattt ttctatgtat tttaaatgta tatggctgtt taatctttga agcatttgg 1081
gcttaagatt gccagcagca cacatcagat gcagtcattg ttgctatcag tgtggaattt 1141
gatagagtct agactcgggc cacttggagt tgtgtactcc aaagctaagg acagtgatga 1201
ggaagatggc agtggccacc ggaggactgg agcagtccct cctcatggcg gcctgtgacc 1261
aaggtcgggg aggagtggag ctatccttcc atgatctgat catgtacagt tccctttta 1321
aaaagcaata aatgcttggg attagaattt ctaacatttt tagtctatca tttaaaacaa 1381
acatttgtat atatacattt gtttatatac atacatgctt ccattctaca aacactgaaa 1441
gaatatttta ttatgggaaa ttccatacac ccaatacccc tggtgagtcc catataccca 1501
gtaccctgtt caacaatcat taactcatgg ccagtcctgc ttcatcttta tttccattta 1561
cttttcttcat gactcttatt ttgacgcata tactagatat ataatttcat ctataattat 1621
tttagtatgt atctctgaaa gataaagact taaatgacca caatactatt atcactgcaa 1681
tagatttatt tttataaaac tccagaggga aaggttgtta tttttctct atgttgaatt 1741
aaatgctaaa tatctaa
```

FIG. 7

ANTAGONISM AS A THERAPY FOR TDP-43 PROTEINOPATHIES

CROSS REFERENCE TO RELATED APPLICATION(S)

This application is a U.S. National Stage Application filed under 35 U.S.C. § 371 and claim priority to International Application No. PCT/US2021/014541, filed Jan. 22, 2021, which application claims priority to U.S. Provisional Application No. 62/965,152, filed on Jan. 23, 2020, the disclosures of which are incorporated herein by reference in their entirety.

STATEMENT REGARDING FEDERALLY SPONSORED RESEARCH

This invention was made with government support under Grant No. NS0978501 awarded by the National Institutes of Health (NIH) and under Grant No. W81XWH-15-1-0187 awarded by the U.S. Department of Defense (DOD). The government has certain rights in the invention.

TECHNICAL FIELD

The disclosure is directed to methods to prevent and/or treat neurological diseases such as amyotrophic lateral sclerosis (ALS). Compositions useful in the herein described methods are provided.

INCORPORATION BY REFERENCE OF SEQUENCE LISTING

Accompanying this filing is a Sequence Listing entitled, "Sequence-Listing_ST25" created on Jan. 21, 2021 and having 3,324 bytes of data, machine formatted on IBM-PC, MS-Windows operating system. The sequence listing is hereby incorporated by reference in its entirety for all purposes.

BACKGROUND

Amyotrophic lateral sclerosis (ALS) is a fatal paralytic disorder caused by degeneration of motor neurons in the brain and spinal cord. About 90% of ALS is sporadic (SALS) with unknown etiology. Familial ALS (FALS) is genetically heterogeneous and represents around 5 to 10% of ALS.

ALS has many different genetic causes. The causes of ALS are complicated and heterogeneous. In general, ALS is considered to be a complex genetic disorder in which multiple genes in combination with environmental exposures combine to render a person susceptible. More than a dozen genes associated with ALS have been discovered, including, SOD-1 ($Cu^{2+}/Zn^{2+}$ superoxide dismutase), TDP-43 (TARDBP, TAR DNA binding protein-43), FUS (Fused in Sarcoma/Translocated in Sarcoma), ANG (Angiogenin), ATXN2 (Ataxin-2), valosin containing protein (VCP), OPTN (Optineurin) and an expansion of the noncoding $G_4C_2$ hexanucleotide repeat in the chromosome 9, open reading frame 72 (C9ORF72).

SUMMARY

The disclosure provides an oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobase sequences of SEQ ID NOs: 1, 2, or 3. In one embodiment, the nucleobase sequence of the oligonucleotide is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% complementary to any one of SEQ ID NOs: 1, 2 or 3. In another embodiment, the oligonucleotide consists of a single-stranded modified oligonucleotide. In another or further embodiment, the oligonucleotide is complementary to the SYF2 mRNA sequence encoded by the gene sequence of FIG. 7. In still another or further embodiment, at least one internucleoside linkage is a modified internucleoside linkage. In a further embodiment, at least one modified internucleoside linkage is a phosphorothioate internucleoside linkage. In another embodiment, each modified internucleoside linkage is a phosphorothioate internucleoside linkage. In yet another embodiment of any of the foregoing embodiments, at least one internucleoside linkage is a phosphodiester internucleoside linkage. In still another embodiment of any of the foregoing at least one internucleoside linkage is a phosphorothioate linkage and at least one internucleoside linkage is a phosphodiester linkage. In yet another embodiment of any of the foregoing at least one nucleoside comprises a modified nucleobase. In a further embodiment, the modified nucleobase is a methylcytosine, methyladenosine, methylguanine, and/or methyluracil. In still another embodiment of any of the foregoing, at least one nucleoside of the modified oligonucleotide comprises a modified sugar. In a further embodiment, the at least one modified sugar is a bicyclic sugar. In yet a further embodiment, the bicyclic sugar comprises a 4'-CH(R)-0-2' bridge wherein R is, independently, H, $C_{1-12}$ alkyl, or a protecting group. In a yet a further embodiment, R is methyl. In another embodiment, R is H. In another embodiment, the at least one modified sugar comprises a 2'-O-methoxyethyl group. In yet another embodiment of any of the foregoing, the oligonucleotide comprises: a gap segment consisting of 8 to 12 linked deoxynucleosides; a 5' wing segment consisting of 3 to 5 linked nucleosides; and a 3' wing segment consisting of 3 to 5 linked nucleosides; wherein the gap segment is positioned between the 5' wing segment and the 3' wing segment and wherein a nucleoside of each wing segment comprises a modified sugar. In a further embodiment, each nucleoside of each wing segment comprises a modified sugar. In yet a further embodiment of any of the foregoing embodiments, the oligonucleotide consists of 20 linked nucleotides.

The disclosure also provides an antisense oligonucleotide comprising a sequence and/or structure as set forth in Table 1 or Table 2, wherein the sequence or structure is at least 8-22 nucleotide in length and sequences that are at least 98-99% identical thereto and which inhibit the expression of SYF2 gene.

The disclosure also provides a method of treating a subject having a neurological disease, the method including the step of administering to the subject an effective dose of a SYF2 antisense molecule, vector expressing a SYF2 antisense molecule, a SYF2 inhibitory nucleic acid and/or a vector expressing a SYF2 inhibitory nucleic acid. In one embodiment, the SYF2 antisense molecule is an oligonucleotide that is complementary to the mRNA sequence of the SYF2 gene of FIG. 6 or any of the oligonucleotides as described herein. In yet another embodiment, the neurological disease is amyotrophic lateral sclerosis. In yet another embodiment, the antisense molecule restores nuclear localization of TDP-43.

The disclosure also provides a modified oligonucleotide, wherein the modified oligonucleotide is a gapmer consisting of a 5' wing segment, a central gap segment, and a 3' wing segment, wherein: the 5' wing segment consists of 3-5 modified nucleosides, the central gap segment consists of 8-12 nucleosides, and the 3' wing segment consists of 3-5 modified nucleosides; wherein the modified oligonucleotide has the nucleobase sequence of any one of SEQ ID NOs: 1-3. In one embodiment, the 3' and/or 5' wing segments comprise modified nucleobases selected from the group consisting of 2'-OMe, 2'-MOE, LNA, DNA and any combination thereof.

In another embodiment, the disclosure provides a pharmaceutical composition comprising the modified oligonucleotide or antisense molecules of the disclosure and a pharmaceutically acceptable diluent or carrier.

BRIEF DESCRIPTION OF THE DRAWINGS

FIG. 2 shows the Hazard ratio (likelihood of death) of C9-ALS iMN survival when treated with the steroid norgestrel and antisense oligonucleotides to suppress the androgen or progesterone receptor, two receptors activated by norgestrel and other steroid hits. Each condition is compared to the no-norgestrel control. A lower hazard ratio indicates better survival. Mean of 3 biological replicates, log-rank test between each condition and the no-norgestrel control.

FIG. 3A-C shows results using the clue.io web tool developed by the Broad Institute. (A) Connectivity Map analysis identified SYF2 suppression as inducing similar gene expression changes to the androgen hits identified in the phenotypic chemical screen on ALS iMNs. (B) Survival of C9-ALS iMNs treated with a negative control or 3 different SYF2-targeting ASOs. Log-rank test. (C) Hazard ratio (likelihood of iMN death of SYF2 ASO treatment vs. negative control ASO treatment for each line) for 3 control, 3 C9-ALS and 10 sporadic ALS lines. SYF2 ASO treatment rescues survival for all C9-ALS lines 8/10 sporadic ALS lines, and does not increase survival of control lines relative to the negative control ASO. Error bars=95% confidence interval p<0.01, **p<0.0001. n=200 iMNs/condition for (B, C); FTD=frontotemporal dementia.

FIG. 7 provide the gene sequence of SYF2 (SEQ ID NO:4).

DETAILED DESCRIPTION

Figure 1A:
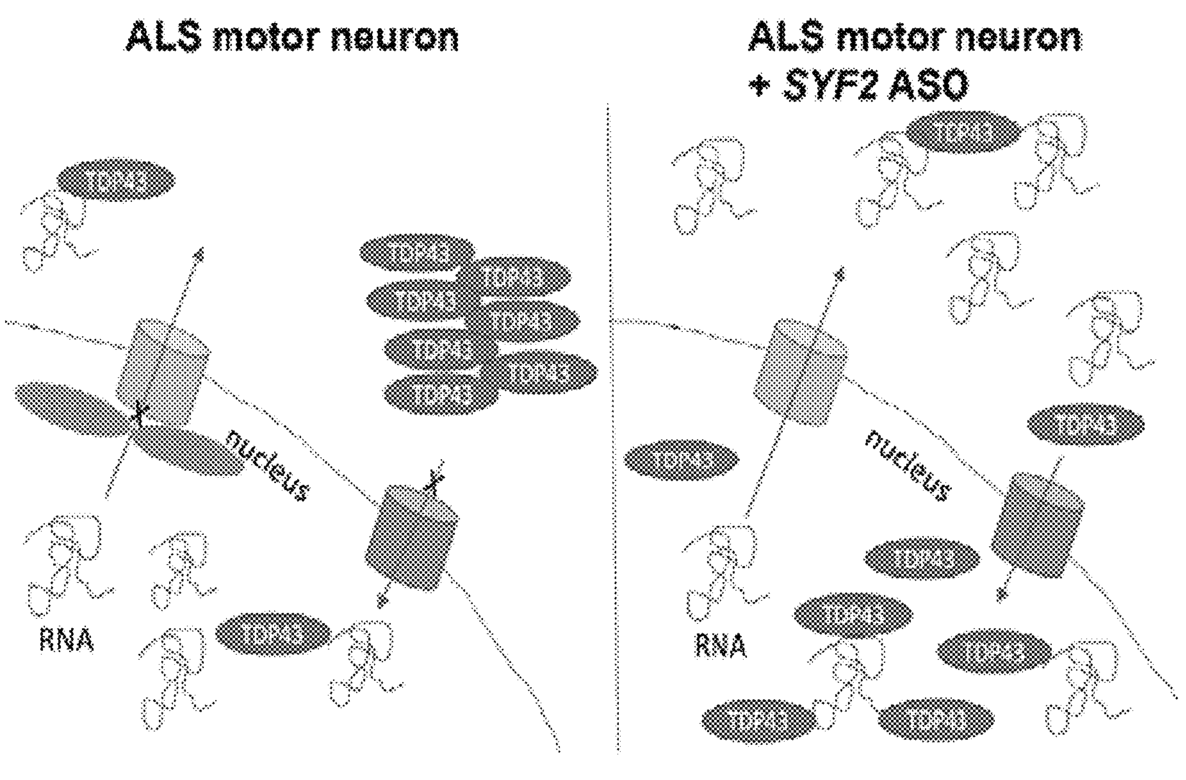
FIG. 1A-F shows (A) A working model of therapeutic mechanism of SYF2 suppression in ALS. SYF2 negatively regulates RNA export from the nucleus, and SYF2 suppression by antisense oligonucleotide (ASO) treatment increases RNA export into the cytoplasm. Higher concentrations of RNA in the cytoplasm prevent TDP-43 aggregation by increasing TDP-43 binding to RNA. This allows monomeric or non-aggregated TDP-43 to enter the nucleus by passive diffusion or active import mechanisms, restoration of the proper nuclear:cytoplasmic TDP-43 ratio, and amelioration of pathogenic gain- and loss-of-function mechanisms of TDP-43. (B,C) Survival of control (CTRL) and C9ORF72 ALS patient (C9-ALS) (B) or sporadic ALS(C) iMNs with a 12-hour pulse treatment of excess glutamate (shown for each individual line separately. N=90 iMNs per line for 3 control, 2 C9-ALS, 6 sALS lines, iMNs quantified from 3 biologically independent iMN conversions per line. Log-rank test. (D) Immunofluorescence analysis of total TDP-43 in control, C9-ALS, or sporadic ALS iMNs. Scale bars=5 um. Dotted lines outline the nucleus and cell body. (E) Overview of phenotypic chemical screen for iMN survival rescue. (F) Heat map depicting results of chemical screen on C9-ALS and sALS iMNs. Each row represents one drug, each column represents iMNs from one patient. Norgestrel and other steroids were broadly-effective drugs (bottom of heat map) that rescued iMN survival from most lines.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

The terms "comprise(s)," "include(s)," "having," "has," "can," "contain(s)," "may" and variants thereof, as used herein, are intended to be open-ended transitional phrases, terms, or words that do not preclude the possibility of additional acts or structures.

The singular forms "a," "an" and "the" include plural references unless the context clearly dictates otherwise.

The present disclosure also contemplates other embodiments "comprising," "consisting of" and "consisting essentially of," the embodiments or elements presented herein, whether explicitly set forth or not.

As used herein, "2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

As used herein, "2'-substituted nucleoside" means a nucleoside comprising a 2'-substituted sugar moiety. As used herein, "2'-substituted" in reference to a sugar moiety means a sugar moiety comprising at least one 2'-substituent group other than H or OH.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number between two points is contemplated with the same degree of precision. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, "antisense molecule", "antisense oligomer", "ASO" or "antisense compound" means an oligomeric nucleic acid or oligomeric duplex capable of achieving at least one antisense activity. An ASO comprises or consists of an oligonucleotide at least a portion of which is complementary to a target nucleic acid (e.g., a nucleic acid encoding SYF2 sequence) to which it is capable of hybridizing, resulting in at least one antisense activity.

As used herein, "antisense activity" means any detectable and/or measurable change attributable to the hybridization of an antisense compound to its target nucleic acid. For example, an antisense activity may include activation of RNase H-dependent degradation of a target nucleic acid, inhibition of splicing of a pre-mRNA transcript, inhibition of polyadenylation of a pre-mRNA transcript, and/or inhibition of formation of the 5'-cap of a pre-mRNA transcript.

As used herein, "bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, "chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more stereorandom chiral centers. In certain embodiments, the molecules are modified oligonucleotides. In certain embodiments, the molecules are compounds comprising modified oligonucleotides.

As used herein, "complementary" in reference to an oligonucleotide means that at least 70% of the nucleobases of the oligonucleotide, or one or more regions thereof, and the nucleobases of another nucleic acid or one or more regions thereof, are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include adenine (A) and thymine (T), adenine (A) and uracil (U), cytosine (C) and guanine (G), 5-methylcytosine (mC) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that oligonucleotides are complementary to another oligonucleotide or nucleic acid at each nucleoside of the oligonucleotide.

As used herein, "gapmer" means a modified oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings." Unless otherwise indicated, "gapmer" refers to a sugar motif. Unless otherwise indicated, the sugar moieties of the nucleosides of the gap of a gapmer are unmodified 2'-deoxyfuranosyl. Thus, the term "MOE gapmer" indicates a gapmer having a sugar motif of 2'-MOE nucleosides in both wings and a gap of 2'-deoxynucleosides. Unless otherwise indicated, a MOE gapmer may comprise one or more modified internucleoside linkages and/or modified nucleobases and such modifications do not necessarily follow the gapmer pattern of the sugar modifications. Table 2, below, provides exemplary MOE-gapmers.

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which is defined by two external regions or "wings" and a central or internal region or "gap." The three regions of a gapmer motif include the "5' wing", the "gap" and the "3' wing" which form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, each nucleoside of each wing of a gapmer is a modified nucleoside.

In certain embodiments, the gap of a gapmer comprises 7-12 nucleosides. In certain embodiments, each nucleoside of the gap of a gapmer is an unmodified 2'-deoxynucleoside.

In certain embodiments, the gapmer is a deoxy gapmer. In certain other embodiments, the nucleosides on the gap side of each wing/gap junction are unmodified 2'-deoxy nucleosides and the nucleosides on the wing sides of each wing/gap junction are modified nucleosides. In certain embodiments, each nucleoside of the gap is an unmodified 2'-deoxy nucleoside. In certain embodiments, each nucleoside of each wing of a gapmer is a modified nucleoside.

In certain embodiments, modified oligonucleotides comprise or consist of a region having a fully modified sugar motif. In such embodiments, each nucleoside of the fully modified region of the modified oligonucleotide comprises a modified sugar moiety. In certain embodiments, each nucleoside of the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

"Inhibit" as used herein refers to the ability to substantially antagonize, prohibit, prevent, restrain, slow, disrupt, alter, eliminate, stop, or reverse the progression or severity of the activity of a particular agent (e.g., infectious agent, gene expression etc.) or disease.

As used herein, the term "internucleoside linkage" refers to the covalent linkage between adjacent nucleosides in an oligonucleotide. As used herein "modified internucleoside linkage" means any internucleoside linkage other than a phosphodiester internucleoside linkage. "Phosphorothioate linkage" is a modified internucleoside linkage in which one of the non-bridging oxygen atoms of a phosphodiester internucleoside linkage is replaced with a sulfur atom.

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include, but are not limited to, phosphates, which contain a phosphodiester bond ("P═O") (also referred to as unmodified or naturally occurring linkages), phosphotriesters, methylphosphonates, phosphoramidates, and phosphorothioates ("P═S"), and phosphorodithioates ("HS—P═S"). Representative non-phosphorus containing internucleoside linking groups include, but are not limited to, methylenemethylimino ($—CH_2—N(CH_3)—O—CH_2—$), thiodiester, thionocarbamate (—O—C(═O)(NH)—S—); siloxane ($—O—SiH_2—O—$); and N,N'-dimethylhydrazine ($—CH_2—N(CH_3)—N(CH_3)—$). Modified internucleoside linkages, compared to naturally occurring phosphate linkages, can be used to alter, typically increase, nuclease resistance of the oligonucleotide. Methods of preparation of phosphorous-containing and non-phosphorous-containing internucleoside linkages are well known to those skilled in the art.

Representative internucleoside linkages having a chiral center include, but are not limited to, alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., JACS 125, 8307 (2003); Wan et al. Nuc. Acid. Res. 42, 13456 (2014); Chapter 10 of Locked Nucleic Acid Aptamers in Nucleic Acid and Peptide Aptamers: Methods and Protocols v 535, 2009 by Barciszewski et al., editor Gunter Mayerand; and WO 2017/015555. In certain embodiments, a population of modified oligonucleotides is enriched for modified oligonucleotides having at least one indicated phosphorothioate in the (Sp) configuration.

As used herein, "MOE" means methoxyethyl. "2'-MOE" means a —$OCH_2CH_2OCH_3$ group at the 2' position of a furanosyl ring.

A "neurological disease" is any disease that causes electrical, biochemical, or structural abnormalities in the brain, spine, or neurons. For example, a neurological disease may be a neurodegenerative disease. The neurodegenerative disease may result in motor neuron degeneration, for example. The neurological disease may be amyloid lateral sclerosis, Huntington's disease, Alzheimer's disease, or frontotemporal dementia, for example. Further examples of neurological diseases include, but are not limited to Parkinson's disease, multiple sclerosis, peripheral myopathy, Rasmussen's encephalitis, attention deficit hyperactivity disorder, autism, central pain syndromes, anxiety, and/or depression, for example.

The neurological disease may be associated with aberrant endosomal trafficking. For example, endosomal pathways and endosomes are necessary components for the recycling or breakdown of membrane-bound proteins, trafficking of golgi-associated proteins, and the extracellular release of proteins in exosomes. These processes aid neurotransmission and drive a balance between recycling and degradation of synaptic vesicles or neurotransmitter receptors, for example.

The neurological disease may be associated with aberrant lysosome degradation. Alterations in the lysosome degradation may be present in the neurological disease, such as a neurodegenerative disease. Cathepsin imbalance during aging and age-related diseases may provoke deleterious effects on CNS neurons and lysosomes may be sites for the unfolding and partial degradation of membrane proteins or their precursors that subsequently become expelled from a cell, or are released from dead cells and accumulate as pathological entities.

Neurodegenerative diseases result in the progressive destruction of neurons that affects neuronal signaling. For example, a neurodegeneration may be amyotrophic lateral sclerosis, Alzheimer's disease, Huntington's disease, Friedreich's ataxia, Lewy body disease, Parkinson's disease, spinal muscle atrophy, primary lateral sclerosis, progressive muscle atrophy, progressive bulbar palsy, and pseudobulbar palsy.

Diseases associated with motor neuron degeneration may be a condition that results in the progressive destruction of motor neurons that interferes with neuronal signaling to the muscles, leading to muscle weakness and wasting. In healthy individuals, upper motor neurons transmit signals from the brain to lower motor neurons in the brain stem and spinal cord, which then transmit the signal to the muscles to result in voluntary muscle activity. The destruction of upper and lower motor neurons affects activity such as breathing, talking, swallowing, and walking, and overtime these functions can be lost. Examples of motor neuron diseases include, but are not limited to, amyotrophic lateral sclerosis, primary lateral sclerosis, progressive muscle atrophy, progressive bulbar palsy, and pseudobulbar palsy. The etiology of disease associated with motor neuron degeneration has not been fully elucidated and has been attributed to genetic factors and sporadic cases.

Neuronal hyperexcitability may occur when receptors for the excitatory neurotransmitter glutamate (glutamate receptors) such as the NMDA receptor and AMPA receptor are over-activated by excess glutamate or by other compounds or neurotransmitters acting on the glutamate receptors. Excitotoxicity may result from neuronal hyperexcitability. Excitotoxicity is the pathological process by which nerve cells are damaged or killed by excessive stimulation. The excessive stimulation allows high levels of calcium ions ($Ca^{2+}$) to enter the cell. $Ca^{2+}$ influx into cells activates a number of enzymes, including phospholipases, endonucleases, and proteases such as calpain. These enzymes can damage cell structures such as components of the cytoskeleton, membrane, and DNA.

Neuronal hyperexcitability may be involved in spinal cord injury, stroke, traumatic brain injury, hearing loss (through noise overexposure or ototoxicity), epilepsy, painful neuropathies, attention deficit hyperactivity disorder, autism, central pain syndrome s, neurodegenerative diseases, multiple sclerosis, Alzheimer's disease, amyotrophic lateral sclerosis (ALS), Parkinson's disease, frontotemporal dementia, schizophrenia, Rasmussen's encephalitis, Huntington's disease, alcoholism or alcohol withdrawal and especially over-rapid benzodiazepine withdrawal, and also Huntington's disease. Other common conditions that cause excessive glutamate concentrations around neurons are hypoglycemia. Blood sugars are the primary glutamate removal method from inter-synaptic spaces at the NMDA and AMPA receptor site.

As used herein, "non-bicyclic modified sugar moiety" means a modified sugar moiety that comprises a modification, such as a substituent, that does not form a bridge between two atoms of the sugar to form a second ring.

As used herein, "nucleobase" means an unmodified nucleobase or a modified nucleobase. As used herein an "unmodified nucleobase" is adenine (A), thymine (T), cytosine (C), uracil (U), and guanine (G). As used herein, a "modified nucleobase" is a group of atoms other than unmodified A, T, C, U, or G capable of pairing with at least one unmodified nucleobase. The terms encompass any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxy-amino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. A universal base is a modified nucleobase that can pair with any one of the five unmodified nucleobases. As used herein, "nucleobase sequence" means the order of contiguous nucleobases in a nucleic acid or oligonucleotide independent of any sugar or internucleoside linkage modification.

In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethylcytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (--C.ident.C--CH.sub.3) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a continuous sequence (i.e., no additional nucleosides are presented between those that are linked).

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound. The term "oligomeric duplex" means a duplex formed by two oligomeric compounds having complementary nucleobase sequences. Each oligomeric compound of an oligomeric duplex may be referred to as a "duplexed oligomeric compound."

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "RNAi compound" which includes "inhibitory nucleic acids" means an antisense compound that acts, at least, in part, through RISC or Ago2 to modulate a target nucleic acid and/or protein encoded by a target nucleic acid. RNAi compounds include, but are not limited to, double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense compounds that act through RNase H.

As used herein, "sugar moiety" means an unmodified sugar moiety or a modified sugar moiety. As used herein, "unmodified sugar moiety" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate. As used herein, modified furanosyl sugar moiety means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars.

In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 4', and/or 5' positions. In certain embodiments one or more non-bridging substituent of non-bicyclic modified sugar moieties is branched. Examples of 2'-substituent groups suitable for non-bicyclic modified sugar moieties include but are not limited to: 2'-F, 2'-$OCH_3$ ("OMe" or "O-methyl"), and 2'-$O(CH_2)_2OCH_3$ ("MOE"). In certain embodiments, 2'-substituent groups are selected from among: halo, allyl, amino, azido, SH, CN, OCN, $CF_3$, $OCF_3$, O—$C_{1-10}$ alkoxy, O—$C_{1-10}$ substituted alkoxy, O—$C_{1-10}$ alkyl, O—$C_{1-10}$ substituted alkyl, S-alkyl, $N(R_m)$-alkyl, O-alkenyl, S-alkenyl, $N(R_m)$-alkenyl, O-alkynyl, S-alkynyl, $N(R_m)$-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)—N(R_m)(R_n)$, where each $R_m$ and $R_n$ is, independently, H, an amino protecting group, or substituted or unsubstituted $C_{1-10}$ alkyl, and the 2'-substituent groups can be further substituted with one or more substituent groups independently selected from among: hydroxyl, amino, alkoxy, carboxy, benzyl, phenyl, nitro ($NO_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), and alkyl. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugar moieties comprise more than one non-bridging sugar substituent, for example, 2'-F-5'-methyl sugar moieties and the like.

In certain embodiments, a 2'-substituted non-bicyclic modified nucleoside comprises a sugar moiety comprising a non-bridging 2'-substituent group selected from: F, $NH_2$, $N_3$, $OCF_3$, $OCH_3$, $O(CH_2)_3NH_2$, $CH_2CH=CH_2$, $OCH_2CH=CH_2$, $OCH_2CH_2OCH_3$, $O(CH_2)_2SCH_3$, $O(CH_2)_2$ $ON(R_m)(R_n)$, $O(CH_2)_2O(CH_2)_2N(CH_3)_2$, and N-substituted acetamide ($OCH_2C(=O)—N(R_m)(R_n)$), where each $R_m$ and $R_n$ is, independently, H, an amino protecting group, or substituted or unsubstituted $C_{1-10}$ alkyl.

In certain embodiments, a 2'-substituted nucleoside non-bicyclic modified nucleoside comprises a sugar moiety comprising a non-bridging 2'-substituent group selected from: F, $OCF_3$, $OCH_3$, $OCH_2CH_2OCH_3$, $O(CH_2)_2SCH_3$, $O(CH_2)_2ON(CH_3)_2$, $O(CH_2)_2O$ $(CH_2)_2N(CH_3)_2$, and $OCH_2C(=O)—N(H)CH_3$ ("NMA").

In certain embodiments, a 2'-substituted non-bicyclic modified nucleoside comprises a sugar moiety comprising a non-bridging 2'-substituent group selected from: F, $OCH_3$, and $OCH_2CH_2OCH_3$.

Certain modified sugar moieties comprise a substituent that bridges two atoms of the furanosyl ring to form a second ring, resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-$CH_2$-2', 4'-$(CH_2)_2$-2', 4'-$(CH_2)_3$-2', 4'-$CH_2$—O-2' ("LNA"), 4'-$CH_2$—S-2', 4'-$(CH_2)_2$—O-2' ("ENA"), 4'-$CH(CH_3)$—O-2' (referred to as "constrained ethyl" or "cEt"), 4'-$CH_2$—O—$CH_2$-2', 4'-$CH_2$—N(R)-2', 4'-CH ($CH_2OCH_3$)—O-2' ("constrained MOE" or "cMOE") and analogs thereof, 4'-$C(CH_3)(CH_3)$—O-2' and analogs thereof, 4'-$CH_2$—$N(OCH_3)$-2' and analogs thereof, 4'-$CH_2$—O—$N(CH_3)$-2', 4'-$CH_2$—$C(H)(CH_3)$-2', 4'-$CH_2$—$C(=CH_2)$-2' and analogs thereof, 4'-$C(R_aR_b)$—N(R)—O-2', 4'-$C(R_aR_b)$—O—N(R)-2', 4'-$CH_2$—O—N(R)-2', and 4'-$CH_2$—N(R)—O-2', wherein each R, $R_a$, and $R_b$, is, independently, H, a protecting group, or $C_{1-12}$ alkyl.

In certain embodiments, such 4' to 2' bridges independently comprise from 1 to 4 linked groups independently selected from: —$[C(R_a)(R_b)]_n$—, —$[C(R_a)(R_b)]_n$—O—, —$C(R_a)=C(R_b)$—, —$C(R_a)=N$—, —$C(=NR_a)$—, —C(=O)—, —C(=S)—, —O—, —$Si(R_a)_2$—, —$S(=O)_x$—, and —$N(R_a)$—; wherein: x is 0, 1, or 2; n is 1, 2, 3, or 4; each $R_a$ and $R_b$ is, independently, H, a protecting group, hydroxyl, $C_{1-12}$ alkyl, substituted $C_{1-12}$ alkyl, $C_{1-12}$ alkenyl, substituted $C_{2-12}$ alkenyl, $C_{2-12}$ alkynyl, substituted $C_{2-12}$ alkynyl, $C_{5-20}$ aryl, substituted $C_{5-20}$ aryl, heterocycle radical, substituted heterocycle radical, heteroaryl, substituted heteroaryl, $C_{5-7}$ alicyclic radical, substituted $C_{5-7}$ alicyclic radical, halogen, $OJ_1$, $NJ_{1-2}$, S $J_1$, $N_3$, $COOJ_1$, acyl (C(=O)—H), substituted acyl, CN, sulfonyl ($S(=O)_2$-$J_1$), or sulfoxyl (S(=O)-$J_1$); and each $J_1$ and $J_2$ is, independently, H, $C_{1-12}$ alkyl, substituted $C_{1-12}$ alkyl, $C_{2-12}$ alkenyl, substituted $C_{2-12}$ alkenyl, $C_{2-12}$ alkynyl, substituted $C_{2-12}$ alkynyl, $C_{5-20}$ aryl, substituted $C_{5-20}$ aryl, acyl (C(=O)—H), substituted acyl, a heterocycle radical, a substituted heterocycle radical, $C_{1-12}$ aminoalkyl, substituted $C_{1-12}$ aminoalkyl, or a protecting group.

Additional bicyclic sugar moieties are known in the art, see, for example: Freier et al., Nucleic Acids Research, 1997, 25(22), 4429-4443, Albaek et al., J. Org. Chem., 2006, 71, 7731-7740, Singh et al., Chem. Commun., 1998, 4, 455-456; Koshkin et al., Tetrahedron, 1998, 54, 3607-3630; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 20017, 129, 8362-8379; Wengel et a., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. patent Publication Nos. Allerson et al., US2008/0039618 and Migawa et al., US2015/0191727.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

As used herein, "target nucleic acid" and "target RNA" mean a nucleic acid that an antisense compound is designed to affect. A target nucleic acid of the disclosure is a nucleic acid which encodes a mammalian SYF2 protein and may for example be a gene, a SYF2 RNA, a mRNA, a pre-mRNA, a mature mRNA or a cDNA sequence. The target may therefore be referred to as an SYF2 target nucleic acid.

For in vivo or in vitro application, the oligonucleotide of the disclosure is typically capable of inhibiting the expression of the SYF2 target nucleic acid in a cell which is expressing the SYF2 target nucleic acid. The contiguous sequence of nucleobases of the oligonucleotide of the disclosure is typically complementary to the SYF2 target nucleic acid, as measured across the length of the oligonucleotide, optionally with the exception of one or two mismatches, and optionally excluding nucleotide based linker regions which may link the oligonucleotide to an optional functional group such as a conjugate, or other non-complementary terminal nucleotides. The target nucleic acid is a messenger RNA, such as a mature mRNA or a pre-mRNA which encodes mammalian SYF2 protein, such as human SYF2, e.g. the human SYF2 sequence, such as that disclosed in FIG. 7.

A "therapeutically effective amount," or "effective dosage" or "effective amount" as used interchangeably herein unless otherwise defined, means a dosage of a drug effective for periods of time necessary, to achieve the desired therapeutic result. An effective dosage may be determined by a person skilled in the art and may vary according to factors such as the disease state, age, sex, and weight of the individual, and the ability of the drug to elicit a desired response in the individual. This term as used herein may also refer to an amount effective at bringing about a desired in vivo effect in an animal, mammal, or human, such as reducing and/or inhibiting the function of a receptor. A therapeutically effective amount may be administered in one or more administrations (e.g., the agent may be given as a preventative treatment or therapeutically at any stage of disease progression, before or after symptoms, and the like), applications or dosages and is not intended to be limited to a particular formulation, combination or administration route. It is within the scope of the present disclosure that the drug may be administered at various times during the course of treatment of the subject. The times of administration and dosages used will depend on several factors, such as the goal of treatment (e.g., treating v. preventing), condition of the subject, etc. and can be readily determined by one skilled in the art.

As used herein, the term "treat" or "treating" a subject, refers to administering a composition or agent described herein to the subject, such that at least one symptom of a disease or disorder is healed, alleviated, relieved, altered, remedied, reduced, ameliorated, or improved. Treating includes administering an amount effective to alleviate, relieve, alter, remedy, reduce, ameliorate, and/or improve one or more symptoms associated with a disease or disorder. The treatment may inhibit deterioration or worsening of a symptom associated with the disease or disorder.

Amyotrophic lateral sclerosis (ALS), an adult-onset neurodegenerative disorder, is a progressive and fatal disease characterized by the selective death of motor neurons in the motor cortex, brainstem and spinal cord. The incidence of ALS is about 1.9 per 100,000. Patients diagnosed with ALS develop a progressive muscle phenotype characterized by spasticity, hyperreflexia or hyporeflexia, fasciculations, muscle atrophy and paralysis. These motor impairments are caused by the denervation of muscles due to the loss of motor neurons. The major pathological features of ALS include degeneration of the corticospinal tracts and extensive loss of lower motor neurons (LMNs) or anterior horn cells, degeneration and loss of Betz cells and other pyramidal cells in the primary motor cortex and reactive gliosis in the motor cortex and spinal cord. ALS is usually fatal within 3 to 5 years after the diagnosis due to respiratory defects and/or inflammation.

A cellular hallmark of ALS is the presence of proteinaceous, ubiquitinated, cytoplasmic inclusions in degenerating motor neurons and surrounding cells. Ubiquitinated inclusions (i.e., Lewy body-like inclusions or Skein-like inclusions) are the most common and specific type of inclusion in ALS and are found in LMNs of the spinal cord and brainstem, and in corticospinal upper motor neurons (UMNs). A few proteins have been identified to be components of the inclusions, including ubiquitin, Cu/Zn superoxide dismutase 1 (SOD1), peripherin and Dorfin. Neurofilamentous inclusions are often found in hyaline conglomerate inclusions (HCIs) and axonal 'spheroids' in spinal cord motor neurons in ALS. Other types and less specific inclusions include Bunnia bodies (cystatin C-containing inclusions) and Crescent shaped inclusions (SCIs) in upper layers of the cortex. Other neuropathological features seen in ALS include fragmentation of the Golgi apparatus, mitochondrial vacuolization and ultrastructural abnormalities of synaptic terminals.

In addition, in frontotemporal dementia ALS (FTD-ALS) cortical atrophy (including the frontal and temporal lobes) is also observed, which may cause cognitive impairment in FTD-ALS patients.

ALS is a complex and multifactorial disease and multiple mechanisms hypothesized as responsible for ALS pathogenesis include, but are not limited to, dysfunction of protein degradation, glutamate excitotoxicity, mitochondrial dysfunction, apoptosis, oxidative stress, inflammation, protein misfolding and aggregation, aberrant RNA metabolism, and altered gene expression.

About 10%-15% of ALS cases have family history of the disease, and these patients are referred to as familial ALS (fALS) or inherited patients, commonly with a Mendelian dominant mode of inheritance and high penetrance. The remainder (approximately 85%-95%) is classified as sporadic ALS (sALS), as they are not associated with a documented family history, but instead are thought to be due to other risk factors including, but not limited to environmental factors, genetic polymorphisms, somatic mutations, and possibly gene-environmental interactions. In most cases, familial (or inherited) ALS is inherited as autosomal dominant disease, but pedigrees with autosomal recessive and X-linked inheritance and incomplete penetrance exist. Sporadic and familial forms are clinically indistinguishable suggesting a common pathogenesis. The precise cause of the selective death of motor neurons in ALS remains elusive.

Recently, an exploration into genetic causes of ALS has discovered mutations in more than 10 different genes that are known to cause fALS. The most common ones are found in the genes encoding Cu/Zn superoxide dismutase 1 (SOD1; ~20%), fused in sarcoma/translated in liposarcoma (FUS/TLS; 1-5%) and TDP-43 (TARDBP; 1-5%). Recently, a hexanucleotide repeat expansion $(G_4C_2)_n$ in the C9orF72 gene was identified as the most frequent cause of fALS (~40%) in the Western population (reviewed by Renton et al., Nat. Neurosci., 2014, 17, 17-23).

Based upon a study of particular therapeutics and their biological activity, antisense oligonucleotide (ASOs) were identified that provide a method of selective therapy for ALS.

The disclosure provides oligonucleotide molecules that inhibit ALS and/or ALS progression. The oligonucleotides are inhibitors of SYF2.

The disclosure provides SYF2 antisense or inhibitory nucleic acids that can inhibit the expression and thus the activity associate with SYF2. The SYF2 antisense or inhibitory nucleic acids can include one or any combination of the oligonucleotides set forth in Table 1 or 2 and sequences that are 95%-99% identical thereto. As mentioned above, the oligonucleotides of the disclosure can comprise modified nucleosides as well as non-modified nucleosides. In addition, the disclosures comprise oligonucleotides that consist of a sequence of SEQ ID NO:1, 2, or 3 operably linked to other oligonucleotides at the 5' and/or 3' ends.

The disclosure provides oligonucleotides (modified or unmodified) that can be used to modulate SYF2 expression. Table 1 provides (5' to 3') sequences useful in designing SYF2 antisense or inhibitory nucleic acids of the disclosure:

TABLE 1

| Sequence ID number | Sequence |
|---|---|
| 1 | AGUCUCTGTTCGCGCUUCUG |
| 2 | CUCCUCCGCGCTGTCCACCA |
| 3 | CUUCUCCTCTTGCCGCACAU |

Sequences as above wherein "U" can be "T" or vice-a-versa

It will be readily apparent that the oligonucleotides provided in Table 1 can be modified at the sugar and/or base level. Moreover, depending upon the delivery mechanism used (e.g., direct deliver or via vector) the sequences can be modified for transcription from a DNA or RNA vector system.

In one embodiment, the disclosure provides modified oligonucleotides consisting of 12-30 linked nucleosides and having a nucleobase sequence comprising at least 8, at least 9, at least 10, at least 11 at least 12, at least 13, at least 14, at least 15, at least 16, at least 17, at least 18, at least 19 or 20 consecutive nucleotide bases of any of the nucleobase sequences of SEQ ID NO:1, 2 or 3 in Table 1. In some embodiments, the modified oligonucleotide is at least 80% to 100% (i.e., 80%, 82%, 84%, 86%, 88%, 90%, 92%, 94%, 96%, 98% or 100%; or any numerical range or value between any of the foregoing values) identical to any of the sequences comprising or consisting of SEQ ID NO:1, 2 or 3.

The sequences provided in Table 1 can be used to design antisense molecules for inhibition of SYF2 expression. For example, gapmer oligonucleotides can be designed using the sequences in Table 1 and can comprise a 5'-wing of about 3-5 nucleotides, a 3'-wing of about 3-5 nucleotides and a gap region comprising 8-20 consecutive deoxyribonucleosides of any one of the sequences of Table 1. In one embodiment, an oligonucleotide of the disclosure comprises a gapmer having a gap segment of at least 8, at least 9, at least 10, at least 11 at least 12, at least 13, at least 14, at least 15, at least 16, at least 17, at least 18, at least 19 or at least 20 consecutive nucleotide bases of any of the nucleobase sequences of SEQ ID NO:1, 2 or 3 in Table 1; flanked by a 5' and 3' wing segments, wherein the gap segment is located between the 5' and 3' wing segments and wherein each of the wing segments comprises a modified sugar or nucleobase. In one embodiment, the gap segment is 8-12 (e.g., 8, 9, 10, 11, or 12) nucleosides in length and each wing segment is 1-5 (e.g., 2-5, 3-5, 4-5, 1-2, 2-3, 1, 2, 3, 4, or 5) modified nucleosides in length. In yet another embodiment, an oligonucleotide of the disclosure comprises a 5' wing segment comprising modified sugars and having the nucleobase sequence of the first 3-5 nucleobases of any of SEQ ID NO:1-3, followed by a gap of the next 8-12 unmodified nucleotides of the same sequence corresponding to SEQ ID NO:1, 2 or 3, followed by a 3' wing segment comprising modified sugars and having the nucleobase sequence of the last 3-5 nucleobases of the same sequence corresponding to SEQ ID NO:1, 2 or 3. Table 2 provides exemplary ASOs of the disclosure.

The 5' and/or 3' wings can comprise the following chemistries: 2'-OMe, 2'-MOE, LNA or DNA, by themselves or used in combination with one another. The backbone linkage of the 5' and/or 3' wings can be phosphorothioate or a mixture of phosphodiester and phosphorothioate. Linkages in the gap region can be phosphorothioate.

In some embodiments, the oligonucleotide is single stranded. In some embodiments the oligonucleotide comprises or is complexed with a moiety that neutralizes charge on the oligonucleotide to promote uptake and transfer across a cell membrane. For example, protein transduction domain (PTDs; sometimes referred to as cell penetrating peptides (CPPs)). Other moieties to promote uptake of naked nucleic acids include modifications to the oligonucleotide backbone. For example, see U.S. Pat. Publ. No: US-2015-0238516-A1, which is incorporated herein by reference, describes a number of nucleobase modifications and fusion constructs useful for oligonucleotide transduction.

TABLE 2

| Antisense Oligonucleotide Sequences (ASOs). (Gapmer design: 5'-five 2'-methoxyethylribose nucleotides-ten DNA nucleotides-five 2'-methoxyethylribose nucleotides-3'; /i2MOErN/ = 2'-methoxyethylribose nucleotide; A, C, T, G = adenine, cytosine, thymine, guanosine, respectively; * = phosphorothioate linkages |
|---|
| SYF2 ASO-1 |
| 5'-mA*mG*mU*mC*mU*C*T*G*T*T*C*G*C*G*C*mU*mU*mC*mU*mG (SEQ, ID NO: 1) |
| SYF2 ASO-2 |
| 5'-mC*mU*mC*mC*mU*C*C*G*C*G*C*T*G*T*C*mC*mA*mC*mC*mA-3' (SEQ ID NO: 2) |
| SYF2 ASO-3 |
| 5'-mC*mU*mU*mC*mU*C*C*T*C*T*T*G*C*C*G*mC*mA*mC*mA*mU-3' (SEQ ID NO: 3) |

The disclosure also provides methods of treating a subject with inhibitory nucleic acids of the disclosure (e.g., ASOs) that inhibit SYF2 activity. In some embodiments, the subject is known to have a neurological disorder associated with TDP-43. In other embodiments a health care professional may diagnose a subject as having a disease associated with motor neuron degeneration by the assessment of one or more symptoms of motor neuron degeneration. To diagnose a neurological disease, a physical exam may be followed by a thorough neurological exam. The neurological exam may assess motor and sensory skills, nerve function, hearing and speech, vision, coordination and balance, mental status, and changes in mood or behavior. Non-limiting symptoms of a disease associated with a neurological disease may be weakness in the arms, legs, feet, or ankles; slurring of speech; difficulty lifting the front part of the foot and toes; hand weakness or clumsiness; muscle paralysis; rigid muscles;

involuntary jerking or writing movements (chorea); involuntary, sustained contracture of muscles (dystonia); bradykinesia; loss of automatic movements; impaired posture and balance; lack of flexibility; tingling parts in the body; electric shock sensations that occur with movement of the head; twitching in arm, shoulders, and tongue; difficulty swallowing; difficulty breathing; difficulty chewing; partial or complete loss of vision; double vision; slow or abnormal eye movements; tremor; unsteady gait; fatigue; loss of memory; dizziness; difficulty thinking or concentrating; difficulty reading or writing; misinterpretation of spatial relationships; disorientation; depression; anxiety; difficulty making decisions and judgments; loss of impulse control; difficulty in planning and performing familiar tasks; aggressiveness; irritability; social withdrawal; mood swings; dementia; change in sleeping habits; wandering; change in appetite.

Tests may be performed to rule diseases and disorders that may have symptoms similar to those of neurological diseases, measure muscle involvement, assess neuron degeneration. Non-limiting examples of tests are electromyography (EMG); nerve conduction velocity study; laboratory tests of blood, urine, or other substances; magnetic resonance imaging (MRI); magnetic resonance spectroscopy; muscle or nerve biopsy; transcranial magnetic stimulation; genetic screening; x-rays; fluoroscopy; angiography; computed tomography (CT); positron emission tomography; cerebrospinal fluid analysis; intrathecal contrast-enhanced CT scan; electroencephalography; electronystagmography; evoked response; polysomnogram; thermography; and ultrasound. A health care professional may also assess the patient's family history of diseases associated with motor neuron degeneration and make a diagnosis in part based on a familial history of neurological diseases. A healthcare professional may diagnose a disease associated with neurological disease in a subject after the presentation of one or more symptoms.

The methods of treatment may comprise administering to a subject in need thereof a composition comprising an effective amount of one or more antisense oligonucleotides or inhibitory oligonucleotides that treats neurological diseases by inhibiting SYF2 expression. The one or more antisense oligonucleotides or inhibitory oligonucleotides may decrease or inhibit neurodegeneration. The one or more antisense oligonucleotides or inhibitory oligonucleotides may decrease neuronal hyperexcitability.

Methods of treatment may include any number of modes of administering a disclosed composition. Modes of administration may include aqueous, lipid, oily or other solutions, emulsions such as oil-in-water emulsions, liposomes, aqueous or oily suspensions and the like. Typically an ASO of the disclosure will be administered directly to the CNS of the subject. Accordingly, the formulation or composition will be sterile and more typically be suitable for injection. The following formulations and methods are merely exemplary and are in no way limiting.

Formulations suitable for parenteral administration include aqueous and non-aqueous, isotonic sterile injection solutions, which may contain anti-oxidants, buffers, bacteriostats, and solutes that render the formulation isotonic with the blood of the intended recipient, and aqueous and non-aqueous sterile suspensions that may include suspending agents, solubilizers, thickening agents, stabilizers, and preservatives. The formulations may be presented in unit-dose or multi-dose sealed containers, such as ampules and vials, and may be stored in a freeze-dried (lyophilized) condition requiring only the addition of the sterile liquid excipient, for example, water, for injections, immediately prior to use. Extemporaneous injection solutions and suspensions may be prepared from sterile powders, granules, and tablets.

Additional therapeutic agent(s) may be administered simultaneously or sequentially with the disclosed one or more antisense or inhibitory nucleic acids and compositions. Sequential administration includes administration before or after the disclosed one or more antisense or inhibitory nucleic acids or compositions. In some embodiments, the additional therapeutic agent or agents may be administered in the same composition as the disclosed one or more antisense or inhibitory nucleic acids. In other embodiments, there may be an interval of time between administration of the additional therapeutic agent and the disclosed one or more antisense or inhibitory nucleic acids. In some embodiments, administration of an additional therapeutic agent with a disclosed one or more antisense or inhibitory nucleic acids may allow lower doses of the other therapeutic agents and/or administration at less frequent intervals. When used in combination with one or more other active ingredients, the one or more antisense or inhibitory nucleic acids of the disclosure and the other active ingredients may be used in lower doses than when each is used singly. Accordingly, the pharmaceutical compositions of the disclosure include those that contain one or more other active ingredients, in addition to one or more antisense or inhibitory nucleic acids of the disclosure. The above combinations include combinations of one or more antisense or inhibitory nucleic acids of the disclosure not only with one other active compound, but also with two or more other active compounds. For example, the compound of the disclosure may be combined with a variety of drugs to treat neurological diseases.

The disclosed one or more antisense or inhibitory nucleic acids can be combined with the following, but are not limited to the following: anticholinergic drugs, anticonvulsants, antidepressants, benzodiazepines, decongestants, muscle relaxants, pain medications, and/or stimulants. Additional types of therapy and treatment include, but are not limited to digital communication devices, feeding tubes, mechanical ventilation, nutritional support, deep brain stimulation, occupational therapy, physical therapy, and/or speech therapy.

The disclosed composition(s) may be incorporated into a pharmaceutical composition suitable for administration to a subject (such as a patient, which may be a human or non-human). The pharmaceutical compositions may comprise a carrier (e.g., a pharmaceutically acceptable carrier). Any suitable carrier can be used within the context of the disclosure, and such carriers are well known in the art. The choice of carrier will be determined, in part, by the particular use of the composition (e.g., administration to an animal) and the particular method used to administer the composition. Accordingly, there is a wide variety of suitable formulations of the composition of the present invention.

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of one or more antisense or inhibitory nucleic acids of the disclosure are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants may also be present in the composition, according to the judgment of the formulator.

The route by which the disclosed one or more antisense or inhibitory nucleic acids are administered and the form of the composition will dictate the type of carrier to be used.

The pharmaceutical compositions of the disclosure can be administered in a number of ways depending upon whether local or systemic treatment is desired and upon the area to be treated. Administration can be (a) oral (b) pulmonary, e.g., by inhalation or insufflation of powders or aerosols, including by nebulizer; intratracheal, intranasal, (c) topical including epidermal, transdermal, ophthalmic and to mucous membranes including vaginal and rectal delivery; or (d) parenteral including intravenous, intraarterial, subcutaneous, intraperitoneal or intramuscular injection or infusion; or intracranial, e.g., intrathecal, intra-cerebroventricular, or intraventricular, administration. In one embodiment the antisense or inhibitory nucleic acid is administered IV, IP, orally, topically or as a bolus injection or administered directly in to the target organ. In another embodiment, the antisense or inhibitory nucleic acid is administered intrathecal or intracerebroventricular as a bolus injection.

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, PA) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Compositions and formulations for parenteral, intrathecal, intra-cerebroventricular, or intraventricular administration can include sterile aqueous solutions which can also contain buffers, diluents and other suitable additives such as, but not limited to, penetration enhancers, carrier compounds and other pharmaceutically acceptable carriers or excipients. For example, an intrathecal cerebrospinal fluid (CSF) catheter can be used to deliver antisense formulations of the disclosure. The catheter can be inserted at the L3 or L4 vertebrae. The distal tip of the catheter extends within the intrathecal space to approximately the L1 vertebrae. Antisense oligonucleotides are dissolved in saline, are sterilized by filtration, and are administered at 0.33 ml/min in a 1.0 ml volume followed by a 0.5 ml sterile water flush. Total infusion time is 4.5 min.

Although the amounts of components in the systemic compositions may vary depending on the type of systemic composition prepared, in general, systemic compositions include 0.01% to 50% of active compound and 50% to 99.99% of one or more carriers. Compositions for parenteral administration typically include 0.1% to 10% of actives and 90% to 99.9% of a carrier including a diluent and a solvent.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

In vivo testing of candidate antisense or inhibitory nucleic acids may be conducted by means known to one of ordinary skill in the art. For example, the candidate one or more antisense or inhibitory nucleic acids may be administered to a mammal, such as a mouse or a rabbit (as described in the examples herein). The composition may be administered to the mammal by any route deemed appropriate comprising a dose of a candidate antisense or inhibitory nucleic acids. Conventional methods and criteria can then be used to monitor animals for signs of reduction or improvement of motor neuron activity and/or expression or activity of SYF2 gene or protein, respectively. If needed, the results obtained in the presence of the candidate antisense or inhibitory nucleic acids can be compared with results in control animals that are not treated with the candidate antisense or inhibitory nucleic acids. Dosing studies may be performed in, or in conjunction with, the herein described methods for identifying one or more antisense or inhibitory nucleic acids capable of treating a neurological disease and/or any follow-on testing of candidate antisense or inhibitory nucleic acids in vivo. One of skill in the art of medicine may determine the appropriate dosage of one or more antisense or inhibitory nucleic acids. The dosage may be determined by monitoring the subject for signs of disease inhibition or amelioration. The dosage may be increased or decreased to obtain the desired frequency of treatment. The toxicity and efficacy of one or more antisense or inhibitory nucleic acids may be determined by standard pharmaceutical procedures in cell cultures or experimental animals, e.g. determining the lethal dose to 50% of the population (LD50) and the dose therapeutically effective in 50% of the population (ED50). The dose ratio of LD50/ED50 is the therapeutic index and, indicating the ratio between the toxic and therapeutic effects. A delivery system may be designed to help prevent toxic side effects, by delivering the one or more antisense or inhibitory nucleic acids to specific targets, e.g., delivered specifically to motor or central nervous system neurons. The optimal dose of the one or more antisense or inhibitory nucleic acids may be determined based on results of clinical electrophysiology or electromyography to analyze excitability in peripheral nerves, for example.

The dosage for use in humans may be determined by evaluating data obtained from animal studies and cell culture assays. The preferred dosage will have little or no toxicity and include the ED50. The dosage may vary depending on the dosage form and route of administration. For any antisense or inhibitory nucleic acid used in the methods described herein, the dosage may be estimated initially in cell culture. A dose may be formulated in animal models that includes the concentration of the test compound which achieves a half maximal inhibition of symptoms (LD50) as determined in cell culture. Such information obtained from cell cultures and animal models may be used to more accurately determine useful doses in humans.

Thus, the disclosure provides methods of treating neurodegenerative diseases and disorders associated with TDP-43 expression by administering to the subject a composition comprising one or more of the ASO compositions described herein comprising an ASO containing a sequence of 8-20 consecutive nucleosides of SEQ ID NO:1, 2 or 3.

The present invention has multiple aspects, illustrated by the following non-limiting examples.

EXAMPLES

To identify new therapeutic targets that can address multiple forms of ALS, cellular reprogramming technology was used to generate induced motor neurons (iMNs) from C90RF72 and sporadic ALS patient induced pluripotent stem cells (iPSCs). A phenotypic chemical screen of 4000 approved drugs and bioannotated tool compounds to search for targets that can rescue the degeneration of ALS iMNs.

A heatmap was generated to identify the effect of 40 drugs on iMNs from 3 different C9ORF72 ALS/FTD patients and 8 different sporadic ALS patients. The 40 drugs or small molecules in this experiment were the validated hit compounds from a phenotypic screen of 3000 compounds on C9-ALS induced motor neurons (iMNs). Only about 6 of these drugs were effective on sporadic ALS iMNs. The clustering of the drugs and patient lines was done by unsupervised hierarchical clustering.

Figure 1B:
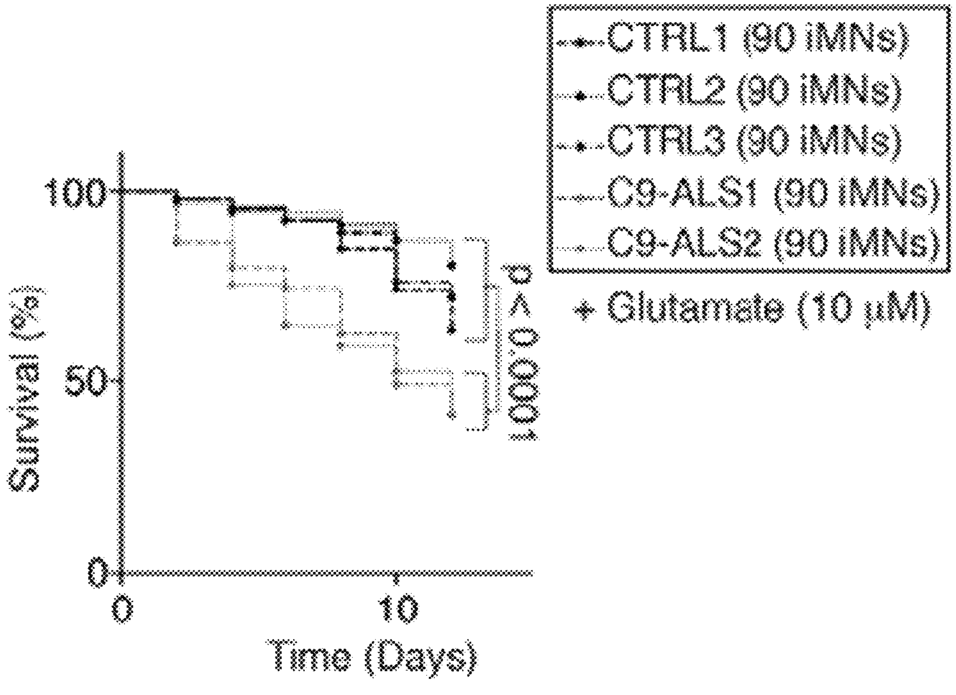
Figure 1C:
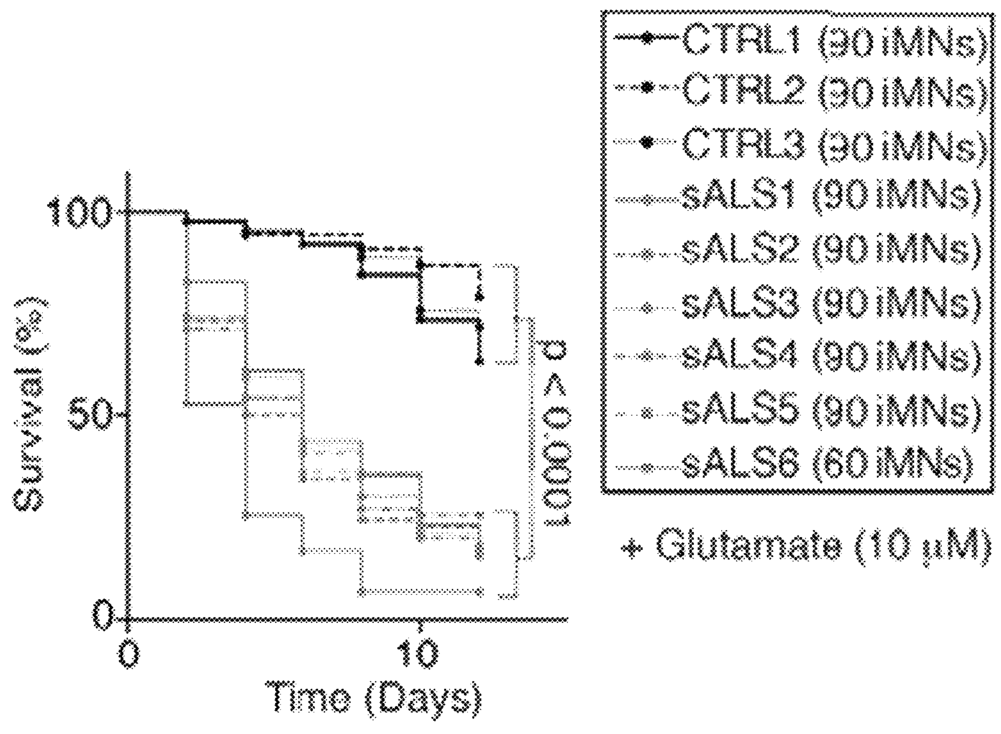
Figure 1D:
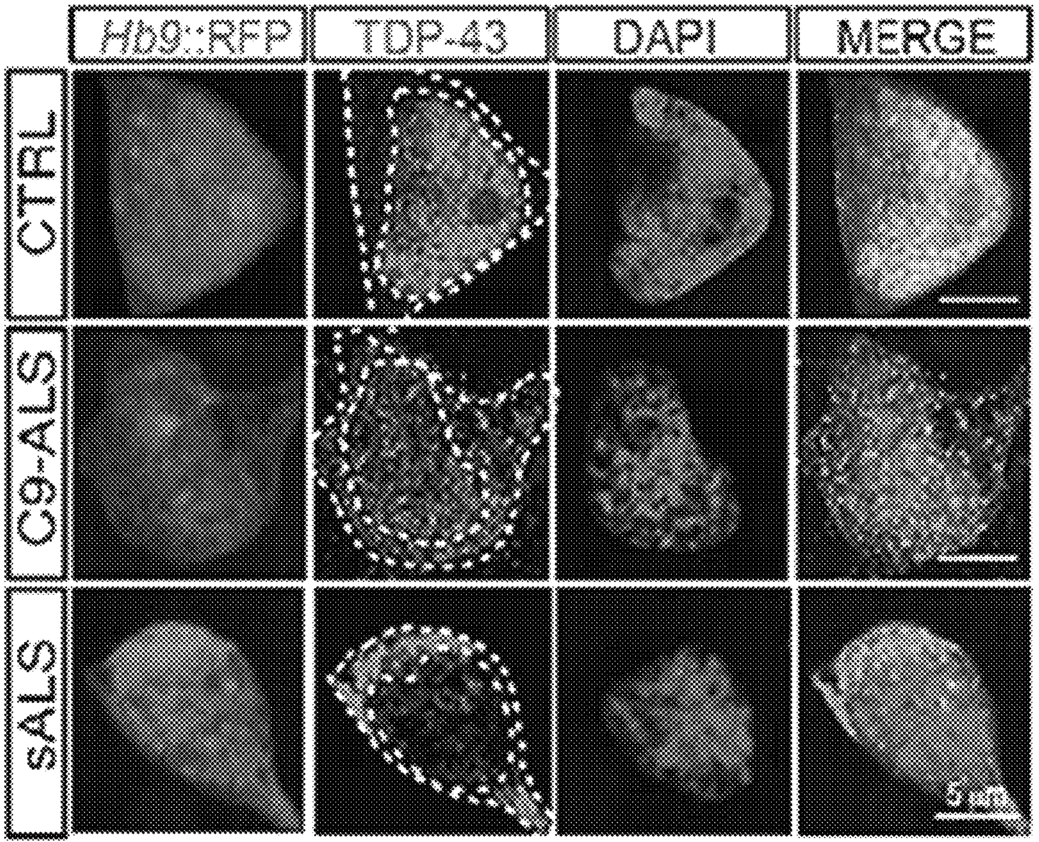
Figures 1E, 1F:
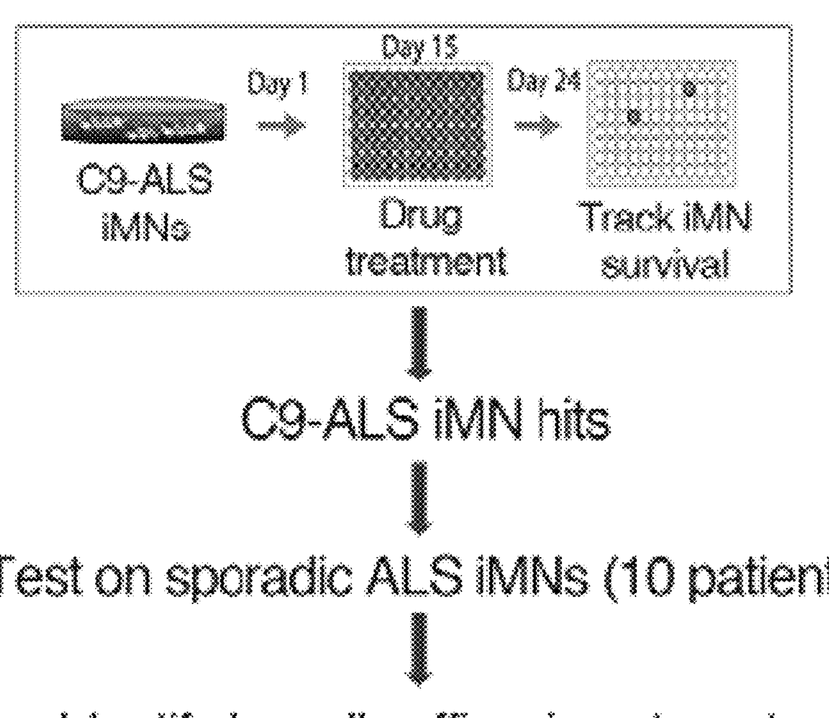
Figures 2, 3A:
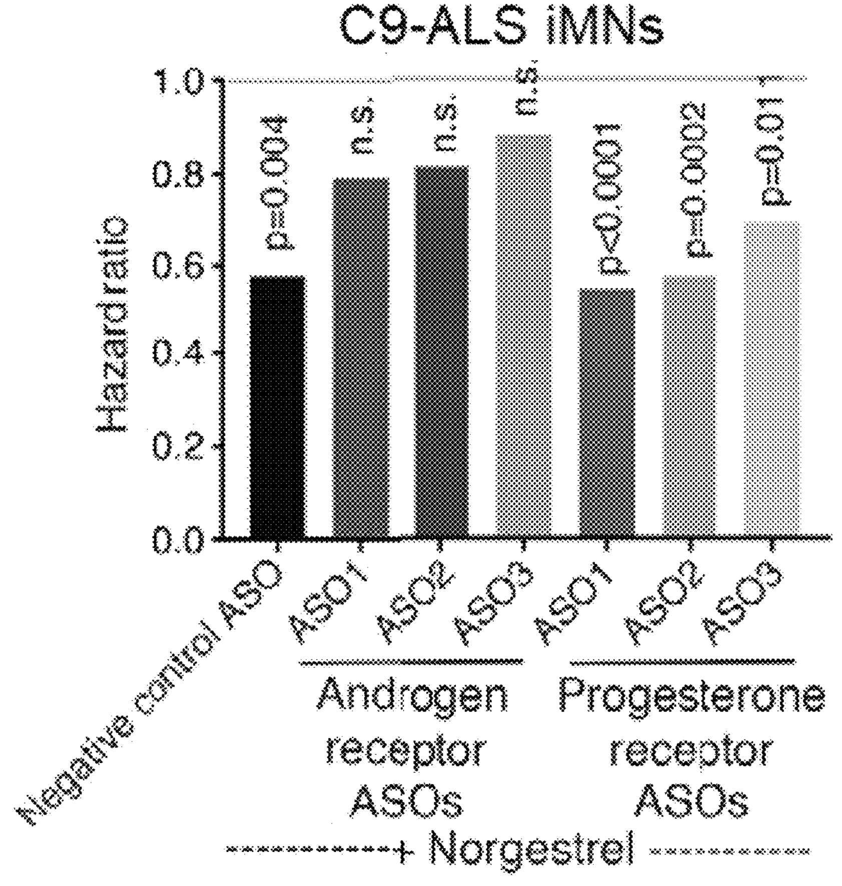

Several steroid drugs that activate androgen receptor signaling were in the group of broadly active drugs. These drugs include norgestrel, exemestane, levonorgestrel, anastrozole, and dihydrotestosterone. FIG. 1B-C and FIG. 2 shows the survival of iMNs from two different C9-ALS patients treated with DMSO (vehicle control) or norgestrel.

Experiments were the performed to verify the therapeutic target of norgestrel since it activates the androgen and progesterone receptors. FIG. 2 shows the hazard ratio of iMN survival. The iMNs were derived from a C9ORF72 ALS/FTD patient and treated with norgestrel+a scrambled negative control ASO. 3 different androgen receptor ASOs, and 3 different progesterone receptor ASOs were tested. Norgestrel+scrambled ASO lowers the likelihood of death, and thus lowers the hazard ratio (see FIG. 2). The progesterone receptor ASOs do not change the effect of norgestrel. However, the androgen receptor ASOs block the therapeutic effect of norgestrel, verifying that activating the androgen receptor is required for rescue and is thus the therapeutic target.

Activating the androgen receptor is not an ideal approach for ALS because 1) there could be undesired side effects upon chronic treatment and 2) there are already existing drugs that do this, making it hard to advance a new drug, bioinformatics was used to identify genes that when suppressed could mimic the effect of androgen receptor activation.

One of the most potent classes of small molecules that showed broad efficacy across C90RF72 and sporadic ALS iMN cultures was bioinformatically predicted to mimic the suppression of a pre-mRNA-binding protein SYF2. Consistent with this notion, ASO-mediated suppression of SYF2 potently rescues the survival of C90RF72 and sporadic ALS iMNs. Moreover, Syf2 ASO treatment rescues motor function in hTDP-43-expressing mice. Thus, unbiased phenotypic screening identified SYF2 suppression as a potent strategy for rescuing the degeneration of ALS motor neurons.

SYF2 binds to pre-mRNA splicing complexes and although it is not essential for splicing, evidence suggests it regulates nuclear export of mRNA. Preliminary data indicate that SYF2 suppression in iMNs increases RNA export, leading to a higher RNA concentration in the cytoplasm. Thus, it was hypothesized that SYF2 suppression rescues ALS iMN degeneration by decreasing TDP-43 aggregation in the cytoplasm and increasing nuclear TDP-43. Consistent with this notion, SYF2 suppression rescues the nuclear: cytoplasmic ratio of TDP-43 in ALS iMNs and impedes optogenetically-induced TDP-43 aggregation in iMNs To this end, the Connectivity Map database (www.clue.io) was used to identify genes whose suppression results in gene expression changes most similar to the 5 androgen receptor agonists identified in the screen. Of the top-ranked genes from this analysis, the gene expression profile induced by SYF2 suppression was most similar to the profiles induced by the androgen receptor agonists (FIG. 3A). Treatment with antisense oligonucleotides (ASOs) targeting the highly-ranked genes from the clue.io analysis showed that SYF2 most potently rescued iMN degeneration and was efficacious on neurons from all 3 C90RF72 ALS and 8/10 sporadic ALS patients (FIG. 3B, C). Importantly, multiple SYF2 ASOs rescued ALS iMN survival, confirming that SYF2 is the relevant target (FIG. 3B). Because mice and humans haplodeficient for SYF2 are normal and ASOs can effectively treat motor neuron diseases, an ASO-mediated suppression of SYF2 was pursued as a therapeutic strategy for C90RF72 and sporadic ALS.

Previous studies suggest that SYF2 regulates recruitment of splicing complexes and RNA export from the nucleus but is not essential for splicing. Studies have demonstrated that SYF2 directly interacts with RNA export complex proteins such as TREX that transport RNA from the nucleus to the cytoplasm. It was hypothesized that SYF2 is a negative regulator of RNA export from the nucleus. Therefore, suppressing SYF2 rescues neurodegeneration by increasing RNA export from the nucleus, thereby increasing cytoplasmic RNA levels, blocking cytoplasmic TDP-43 oligomerization, and increasing TDP-43 levels in the nucleus (FIG. 1).

To determine if SYF2 suppression increases cytoplasmic RNA levels, a 5-hour pulse of 5-Ethynyl Uridine (EU) to label nascent RNA in iMNs treated with a negative control or SYF2 ASO was used.

Figure 4A:
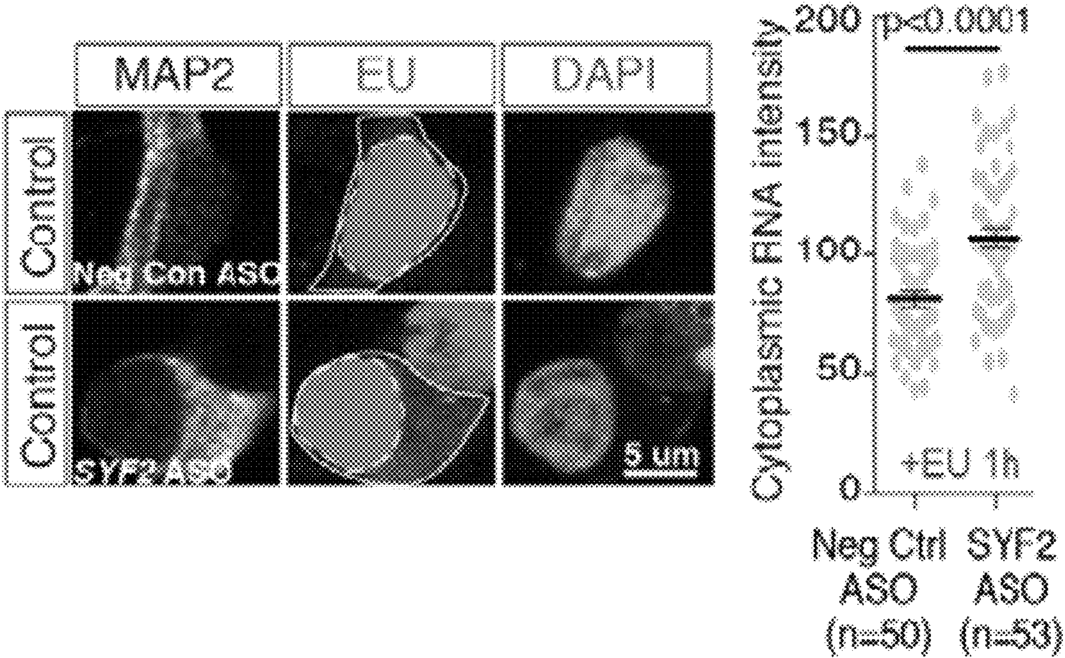
FIG. 4A-H shows suppression increases cytoplasmic RNA and decrease cytoplasmic TDP-43. (A) Images and quantification of cytoplasmic RNA intensity as measured by EU intensity after a 1 hour EU treatment. Neurons were treated with a negative control (Neg Con) or SYF2 ASO for 1 day before EU treatment. Mean±s.e.m. unpaired t-est. n=50 or 53 neurons quantified per condition. Each circle represents and individual neuron, quantified from 2 biological replicates per condition. For (A-C), dotted and solid white lines outline the nucleus and cell body, respectively. (B) Nuclear:cytoplasmic RNA intensity as measured by EU after a 1 hour pulse treatment. Median±interquartile range. Mann-Whitney test. Each circle represents an individual iMN, cells quantified from 2 biological replicates per condition. (C) Images of total TDP-43 immunostaining in control iMNs or C9-ALS iMNs treated with a negative control or SYF2 ASO. (D, E) Nuclear:cytoplasmic ratio of TDP-43 intensity in CTRL and C9-ALS iMNs (D) or C9-ALS iMNs treated with negative control or SYF2 ASOs (E). Each circle represents an individual iMN, cells quantified from 2 biological replicates per condition. Mean±s.e.m., Mann-Whitney (D) or one-way ANOVA (E). (F) Nuclear: cytoplasmic ratio of TDP-43 fluorescence in sporadic ALS iMNs treated with negative control or SYF2 ASOs. Median±interquartile range. Kruskal-Wallis test. Each cycle represents an individual iMN, cells quantified from 2 biological replicates per condition. (G) Size of cytoplasmic Cry2-TDP-43-mCherry aggregates in iMNs exposed to blue light or 12 hours and treated with a negative control or SYF2 ASOs. Mean±s.e.m., One-way ANOVA, Cry2-TDP-43-mCherry in 4 control lines were analyzed. 2500 aggregates/line quantified from 2 biological replicates. (H) Cytoplasmic:nuclear ratio of Cry2-TDP-43-mCherry intensity (soluble and aggregated) in iMNs exposed to blue light for 12 hours and treated with negative control or SYF2 ASOs. Median±interquartile range, Kruskal-Wallis test. Each circle represents an individual iMN, cells quantified from 2 biological replicates per condition. N=2 control iPSC lines.
Figure 4B:
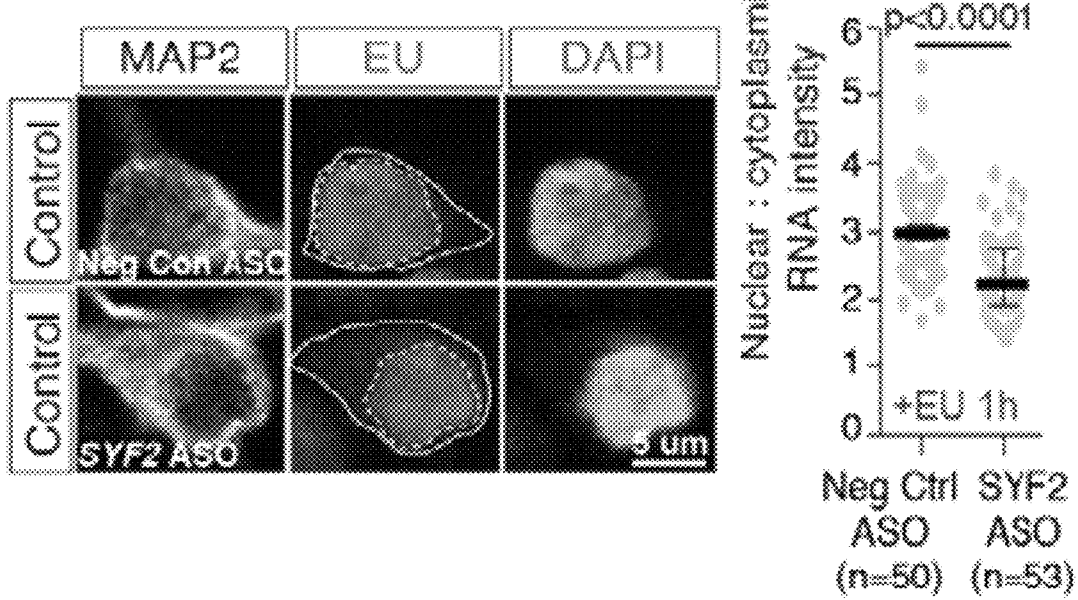
Figure 4C:
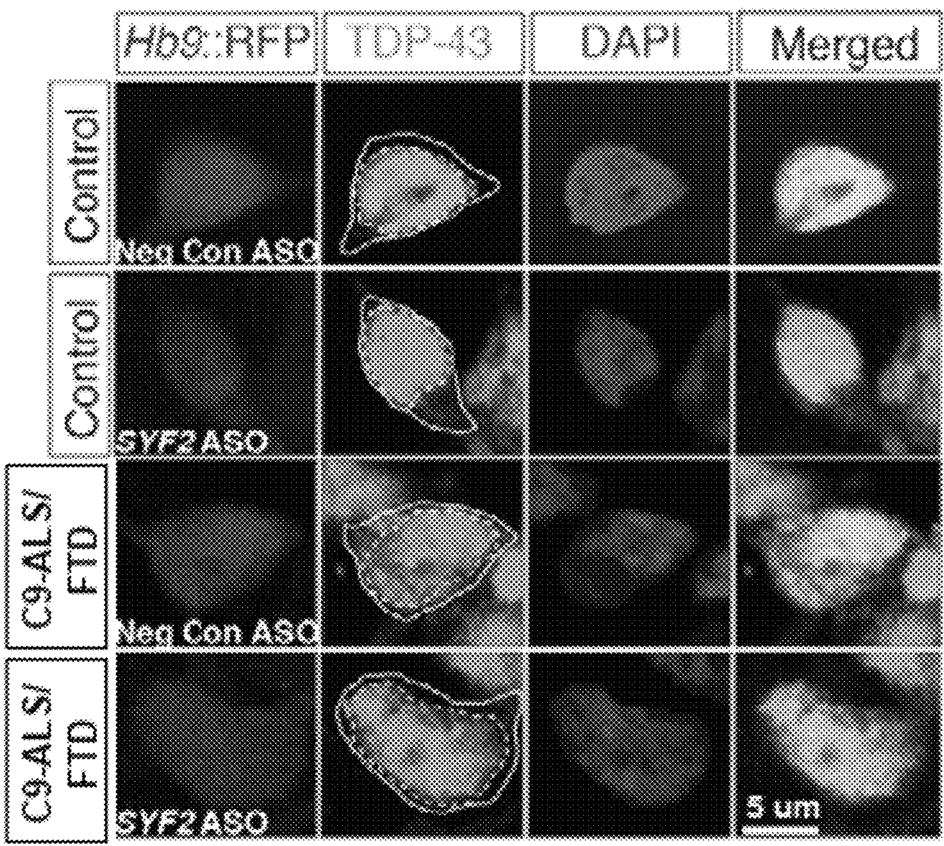
Figure 4D:
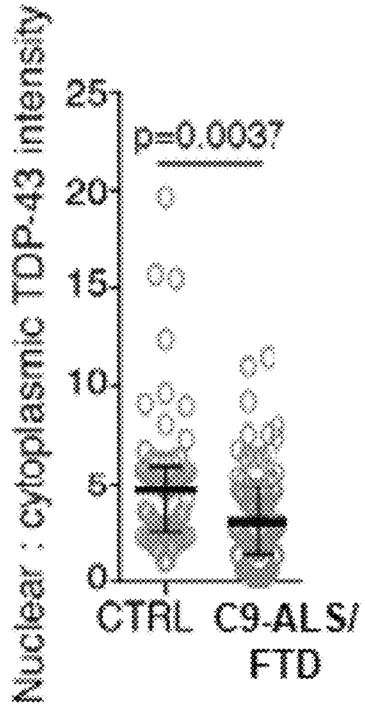
Figure 4E:
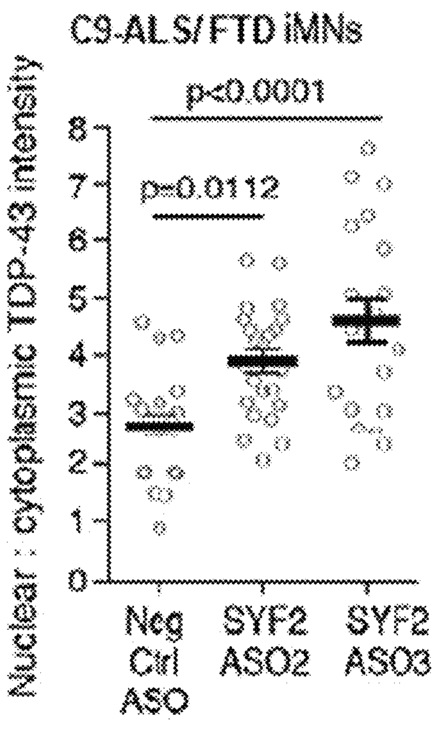
Figure 4F:
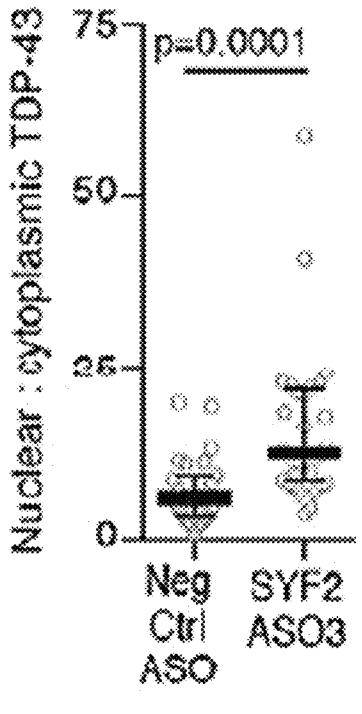

Consistent with the central hypothesis, SYF2 ASO treatment led to a 30; increase in cytoplasmic RNA levels and significantly reduced the nuclear:cytoplasmic ratio of RNA in iMNs (FIG. 4A, B). These data show that SYF2 suppression significantly increases the cytoplasmic RNA concentration in motor neurons.

To determine if SYF2 suppression rescues TDP-43 mislocalization, the nuclear:cytoplasmic ratio of TDP-43 in ALS iMNs treated with negative control or SYF2 ASOs was quantified. SYF2 suppression significantly increased the nuclear:cytoplasmic ratio of TDP-43 in both C90RF72 and sporadic ALS iMNs (FIG. 4C-F). In addition, total RNA-seq analysis of ASO-treated sporadic ALS iMNs showed that SYF2 suppression caused changes in TDP-43 target RNAs known to occur with increased nuclear TDP-43 levels, such as a decrease in VEGFA RNA levels (9.1-fold decrease, p-adjusted=6.6e-36).

Figure 4G:
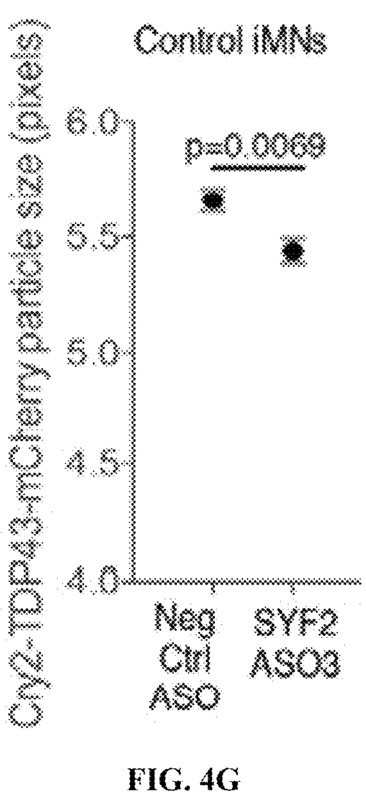
Figure 4H:
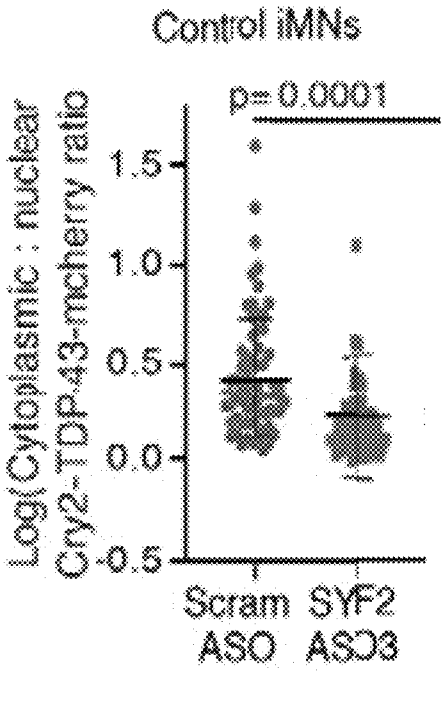

To determine if SYF2 suppression can prevent cytoplasmic TDP-43 aggregation, a Cry2-TDP-43-MCherry fusion protein was expressed in iMNs. Blue light exposure causes Cry2 domains self-oligomerize. Cry2 oligomerization induces aggregation of the tethered TDP-43 domains due to TDP-43's tendency to aggregate at high local concentrations. Though high RNA concentrations impair photo-induced TDP-43 aggregation in the nucleus, aggregation occurs readily in the cytoplasm where the RNA concentration is lower. Several studies have shown that cytoplasmic aggregation of TDP-43 can collect monomeric TDP-43, causing a cytoplasmic accumulation and nuclear depletion of TDP-43. Consistent with this, light activation in iMNs expressing Cry2-TDP-43-mcherry and treated with a negative control ASO rapidly formed cytoplasmic Cry2-TDP-43-MCherry aggregates and showed nuclear depletion of the Cry2-TDP-43-MCherry fusion protein (FIG. 4G). In contrast, SYF2 ASO treatment reduced the light-dependent formation of cytoplasmic Cry2-TDP-43-MCherry aggregates and increased nuclear Cry2-TDP-43-mcherry in iMNs (FIG. 4G, H). Thus, SYF2 suppression reduces cytoplasmic TDP-43 aggregation and rescues TDP-43 mislocalization in ALS iMNs.

These data suggest that SYF2 suppression rescues ALS iMN survival by increasing RNA export, decreasing cytosolic TDP-43 oligomerization, and restoring nuclear TDP-43 localization. This represents a new therapeutic approach that has not been previously tested for ALS.

One potential concern regarding SYF2 suppression as a therapeutic strategy is its impact on splicing. To assess this, a total RNA-seq data set was examined on sporadic ALS iMNs treated with a negative control or SYF2 ASO. The RNA-seq data indicated that SYF2 ASO treatment under the same conditions used for iMN survival and TDP-43 localization experiments reduced SYF2 mRNA levels by 25%. Consistent with SYF2 being dispensable for splicing, iMN treatment with the SYF2 ASO only significantly altered levels of 857 out of 55,084 total RNA transcripts. This is comparable to the number of differentially-expressed transcripts observed with TDP-43 knockdown in human cells, suggesting that changes in nuclear TDP-43 levels could account for many of these changes. Importantly, mice and humans haplodeficient for SYF2 are normal, and the RNA-seq data suggest that <50% knockdown of SYF2 in iMNs is sufficient to elicit the survival, cytoplasmic RNA, and TDP-43 effects observed (FIG. 3B, C, 4A-H).

Figure 5A:
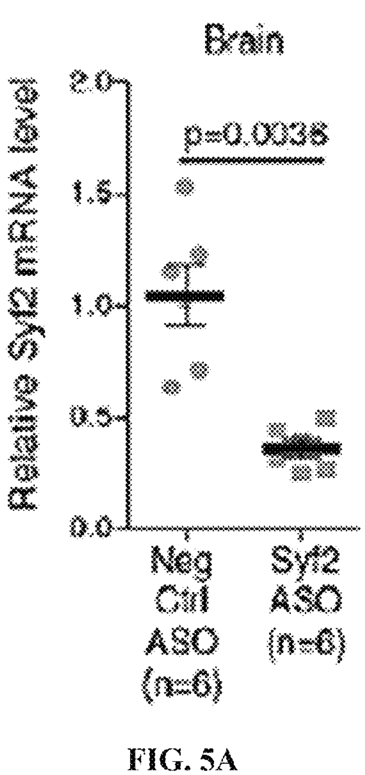
FIG. 5A-D shows Syf2 suppression rescues motor function in TDP-43 mice in vivo. (A) qRT-PCR analysis showing the relative SyF2 mRNA levels in the brains of neonatal mice treated for 72 hours with a negative control or Syf2 ASO. Each data point represents one mouse. Mean±s.e.m. Unpaired t-test with Welch's correction. (B-D) Kyphosis (B), tremor (C), and gait (D) scores in wild-type (WT) or TDP-43 mice treated with 50 ugs of a negative control ASO (NC ASO) or a Syf2 ASO at postnatal day 1. A higher score denotes a more severe motor phenotype. Scoring was performed by an individual blinded to the genotype and treatment of the mice. Mean±s.e.m. at each time point. Unpaired t-test between the TDP-43 NC ASO and Syf2 ASO groups at each time point. *p<0.05, p<0.01, *p<0.001, ****p<0.0001. n-11, 9, 8, and 8 mice per group as denoted in each graph.
Figure 5B:
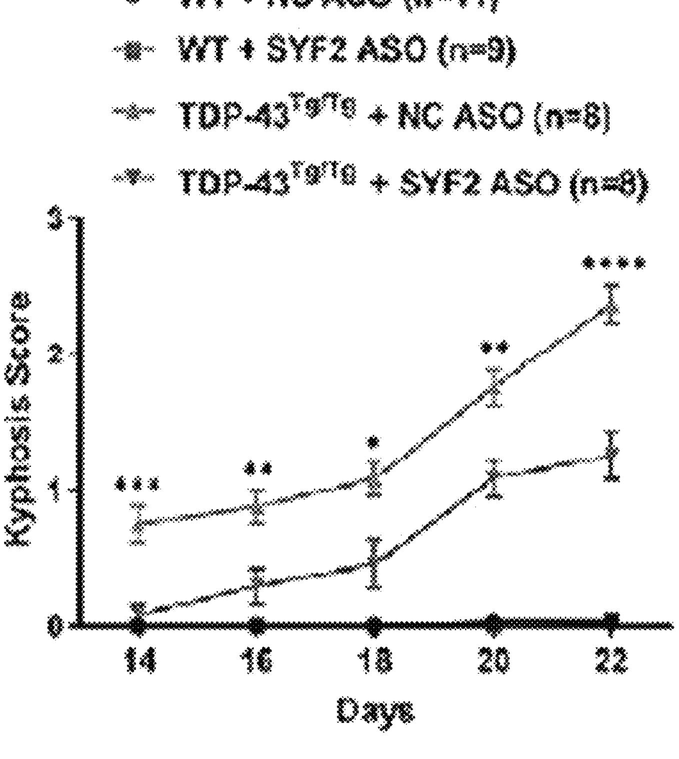
Figures 5C, 5D:
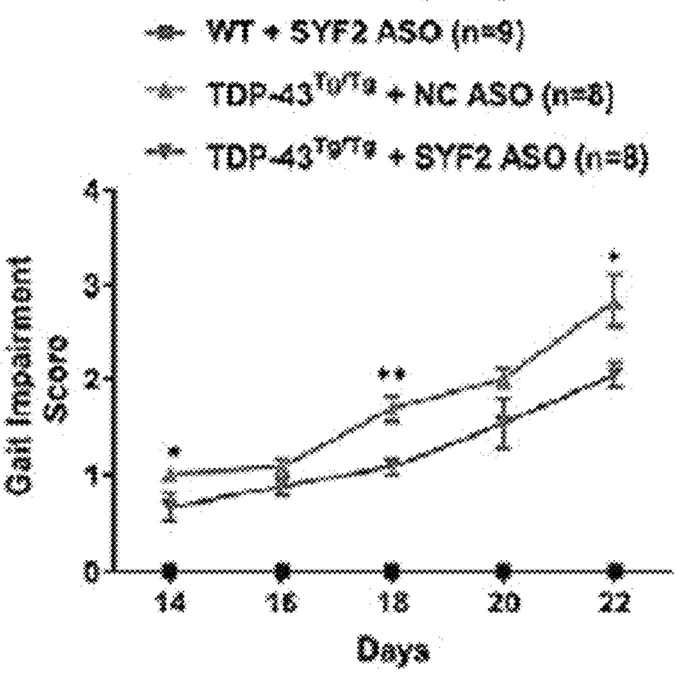

To test the efficacy of Syf2 suppression in vivo, a previously published TDP-43 mouse model was used to test Syf2 suppression in vivo. These Thy1::hTDP-43 mice develop motor deficits, neurodegeneration, paralysis by about day 30 in colony (FIG. 5B-D). Syf2 ASO treatment significantly reduced total brain Syf2 mRNA levels and was well tolerated (FIG. 5A). Compared to a negative control ASO, Syf2 ASO treatment significantly rescued gait, tremor, and kyphosis phenotypes in TDP-43 mice (FIG. 5B-D). The magnitude of motor function rescue upon Syf2 ASO treatment was similar to that observed previously using Atxn2 ASO treatment. Thus, the data suggest that Syf2 suppression can rescue motor deficits caused by TDP-43 proteinopathy in vivo.

Figure 6A:
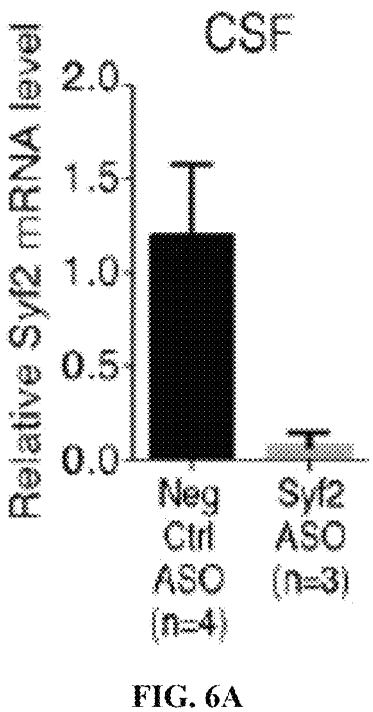
FIG. 6A-B show SYF2 mRNA and protein in CSF may be viable in vivo target engagement biomarkers. (A) qRT-PCR analysis shows in the relative Syf2 mRNA levels in the CSF of neonatal mice treated for 72 hours with 50 ugs of a negative control or syf2 ASO. Mean±s.e.m. n=4 and 3 mice per group. (B) Western blot analysis of SYF2 levels in the CSF of a mouse treated with a negative control ASO for 72 hours.
Figure 6B:
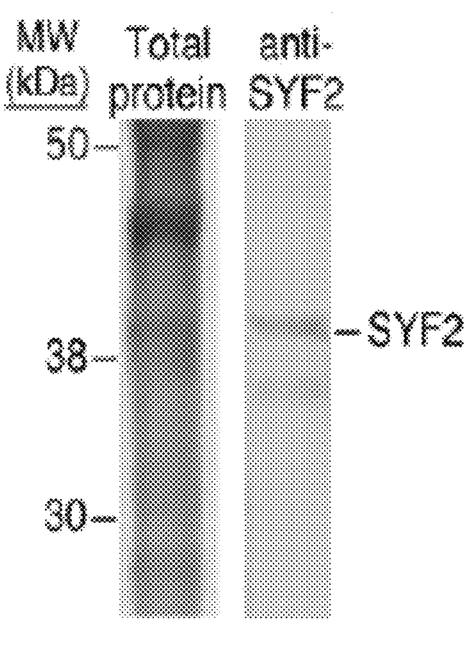
Figure 8:
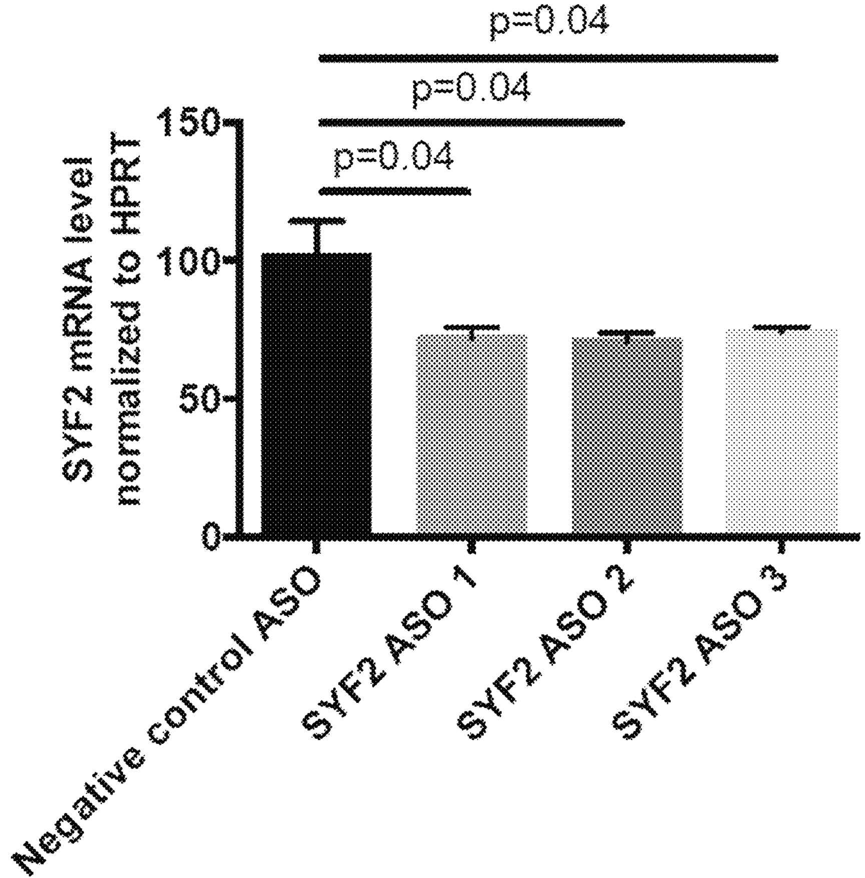
FIG. 8 shows SYF2 ASOs suppress SYF2 mRNA levels in human cells in vitro. SYF2 mRNA levels in cells treated with SYF2 ASO1, 2, or 3 relative to cells treated with a negative control ASO. Hela cells were transfected with 40 nM ASO using lipofectamine 2000 and RNA was harvested 3 days later. qRT-PCR analysis of SYF2 and HPRT mRNA levels was used to determine the level of SYF2 mRNA normalized to the housekeeping gene HPRT. SYF2 ASO1, 2 and 3 significantly reduced SYF2 mRNA levels. Mean+/− s.e.m. One-way ANOVA. N=3 biological replicates per group.

ASO clinical trials for neurological indications have quantified cerebrospinal fluid (CSF) levels of the target mRNA or its protein product to assess target engagement. For example, the SOD1 ASO trials have measured CSF SOD1 levels to assess target engagement. To explore this possibility for SYF2, CSF was extracted from mice 72 hours after injection with 50 ugs of a negative control or Syf2 ASO and assessed Syf2 mRNA levels by qRT-PCR. Syf2 ASO treatment sharply reduced Syf2 mRNA in the CSF, suggesting this could serve as a biomarker of target engagement (FIG. 6A). Using CSF from negative control ASO-injected mice, data show that SYF2 protein was readily detectable in CSF (FIG. 6B). Thus, CSF levels of SYF2 mRNA or protein could act as biomarkers for SYF2 ASO target engagement in vivo.

The disclosure provides ASOs that suppress SYF2 expression in human cells. The accompany data suggest that these ASOs may be capable of preventing neurodegeneration in ALS and FTD patients.

The invention claimed is:

1. A method of treating a human subject having a neurological disease, the method including the step of administering to the subject an effective dose of a human SYF2 antisense molecule that is complementary to the mRNA sequence encoded by the nucleic acid sequence of SEQ ID NO: 4, or a vector expressing the SYF2 antisense molecule, wherein (i) the SYF2 antisense molecule is 12 to 30 nucleotides in length and (ii) the neurological disease is selected from the group consisting of amyotrophic lateral sclerosis (ALS) and frontotemporal dementia (FTD).

2. The method of claim 1, wherein the antisense molecule restores nuclear localization of TDP-43.

3. The method of claim 1, wherein the SYF2 antisense molecule comprises a modified oligonucleotide, wherein the modified oligonucleotide is a gapmer consisting of a 5' wing segment, a central gap segment, and a 3' wing segment, wherein: the 5' wing segment consists of 3-5 modified nucleosides, the central gap segment consists of 8-12 nucleosides, and the 3' wing segment consists of 3-5 modified nucleosides; wherein the modified oligonucleotide has the nucleobase sequence of any one of SEQ ID NOs: 1-3.

4. The method of claim 3, wherein the 3' and/or 5' wing segments comprise modified nucleobases selected from the group consisting of 2'-OMe, 2'-MOE, LNA, DNA and any combination thereof.

5. The method of claim 3, wherein the modified oligonucleotide is formulated with a pharmaceutically acceptable diluent or carrier.

6. The method of claim 1, wherein the SYF2 antisense molecule comprises an oligonucleotide consisting of 12 to 30 linked nucleosides and having a nucleobase sequence comprising at least 12 consecutive nucleobases of any of the nucleobase sequences of SEQ ID NOs: 1, 2 or 3.

7. The method of claim 6, wherein the nucleobase sequence of the oligonucleotide is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% complementary to any one of SEQ ID NOs: 1, 2 or 3.

8. The method of claim 6, wherein the oligonucleotide consists of a single-stranded modified oligonucleotide.

9. The method of claim 6, wherein at least one internucleoside linkage is a modified internucleoside linkage.

10. The method of claim 9, wherein at least one modified internucleoside linkage is a phosphorothioate internucleoside linkage.

11. The method of claim 9, wherein each modified internucleoside linkage is a phosphorothioate internucleoside linkage.

12. The method of claim 6, wherein at least one internucleoside linkage is a phosphodiester internucleoside linkage.

13. The method of claim 6, wherein at least one internucleoside linkage is a phosphorothioate linkage and at least one internucleoside linkage is a phosphodiester linkage.

14. The method of claim 6, wherein at least one nucleoside comprises a modified nucleobase.

15. The method of claim 14, wherein the modified nucleobase is a methylcytosine, methyladenosine, methylguanine, and/or methyluracil.

16. The method of claim 6, wherein at least one nucleoside of the modified oligonucleotide comprises a modified sugar.

17. The method of claim 16, wherein at least one modified sugar is a bicyclic sugar.

18. The method of claim 17, wherein the bicyclic sugar comprises a 4'-CH(R)—O-2' bridge wherein R is, independently, H, $C_{1-12}$ alkyl, or a protecting group.

19. The method of claim 18, wherein R is methyl or H.

20. The method of claim 17, wherein at least one modified sugar comprises a 2'-O-methoxyethyl group.

21. The method of claim 6, wherein the oligonucleotide comprises:

a gap segment consisting of 8 to 12 linked deoxynucleosides;

a 5' wing segment consisting of 3 to 5 linked nucleosides; and a 3' wing segment consisting of 3 to 5 linked nucleosides;

wherein the gap segment is positioned between the 5' wing segment and the 3' wing segment and wherein a nucleoside of each wing segment comprises a modified sugar.

22. The method of claim 21, wherein each nucleoside of each wing segment comprises a modified sugar.

23. The method of claim 6, wherein the oligonucleotide consists of 20 linked nucleosides.

24. The method of claim 1, wherein the SYF2 antisense molecule comprises an antisense oligonucleotide comprising a sequence at least 98% identical to the sequence of any one of SEO ID NOs: 1-3, wherein the antisense oligonucleotide is at least 20 nucleotides in length and which inhibits the expression of SYF2 gene.

* * * * *

```
                              SEQUENCE LISTING


<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide ASO1

<400> SEQUENCE: 1

agucucugtt cgcgcuucug                                                20


<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide ASO2

<400> SEQUENCE: 2

cuccuccgcg ctgtccacca                                                20


<210> SEQ ID NO 3
<211> LENGTH: 20
<212> TYPE: DNA
<213> ORGANISM: Artificial Sequence
<220> FEATURE:
<223> OTHER INFORMATION: Antisense Oligonucleotide ASO3

<400> SEQUENCE: 3

cuucucctct tgccgcacau                                                20


<210> SEQ ID NO 4
<211> LENGTH: 1757
<212> TYPE: DNA
<213> ORGANISM: Homo sapiens

<400> SEQUENCE: 4

cttgttgccg gaagtgggaa gagagaaagg ttgtgatggc ggctatagct gcatccgagg     60

tgctggtgga cagcgcggag gaggggtccc tcgctgcggc ggcggagctg gccgctcaga    120

agcgcgaaca gagactgcgc aaattccggg agctgcacct gatgcggaat gaagctcgta    180

aattaaatca ccaggaagtt gtggaagaag ataaaagact aaaattacct gcaaattggg    240

aagccaaaaa agctcgtttg gagtgggaac taaaggaaga ggaaaagaaa aaggaatgtg    300

cggcaagagg agaagactat gagaaagtga agttgctgga gatcagtgca gaagatgcag    360

aaagatggga gaggaaaaag aagaggaaaa accctgatct gggattttca gattatgctg    420

ctgcccagtt acgccagtat catcggttga ccaagcagat caaacctgac atggaaacat    480

atgagagact gagagaaaaa catggagaag agtttttccc aacatccaat agtcttcttc    540

atggaacaca tgtgccttcc acagaggaaa ttgacaggat ggtcatagat ctggaaaaac    600

agattgaaaa acgagacaaa tatagccgga gacgtcctta taatgatgat gcagatatcg    660

actacattaa tgaaaggaat gccaaattca acaagaaagc tgaaagattc tatgggaaat    720

acacagctga aattaaacag aatttggaaa gaggaacagc tgtctaatcc cttcaagaac    780

tgtttataga agcttgagaa tggggtaaaa atttctgcta gcaaaatcaa gttctttttg    840
```

-continued

```
aaattttatc agtaatccag aatttagtag tccatgcctt ctcactcagc atttagaaat    900

aaaaatgtgg tttcttaaac gtatatcctt tcatgtatat ttccacattt ttgtgcttgg    960

atataagatg tatttcttgt agtgaagttg ttttgtaatc tactttgtat acattctaat   1020

tatattattt ttctatgtat tttaaatgta tatggctgtt taatctttga agcattttgg   1080

gcttaagatt gccagcagca cacatcagat gcagtcattg ttgctatcag tgtggaattt   1140

gatagagtct agactcgggc cacttggagt tgtgtactcc aaagctaagg acagtgatga   1200

ggaagatggc agtggccacc ggaggactgg agcagtccct cctcatggcg gcctgtgacc   1260

aaggtcgggg aggagtggag ctatccttcc atgatctgat catgtacagt tccctttttta   1320

aaaagcaata aatgcttggg attagaattt ctaacatttt tagtctatca tttaaaacaa   1380

acatttgtat atatacattt gtttatatac atacatgctt ccattctaca aacactgaaa   1440

gaatatttta ttatgggaaa ttccatacac ccaatacccc tggtgagtcc catataccca   1500

gtaccctgtt caacaatcat taactcatgg ccagtcctgc ttcatcttta tttccattta   1560

ctttcttcat gactcttatt ttgacgcata tactagatat ataatttcat ctataattat   1620

tttagtatgt atctctgaaa gataaagact taaatgacca caatactatt atcactgcaa   1680

tagatttatt tttataaaac tccagaggga aaggttgtta ttttttctct atgttgaatt   1740

aaatgctaaa tatctaa                                                  1757
```